(12) United States Patent
Woods et al.

(10) Patent No.: US 6,901,352 B2
(45) Date of Patent: May 31, 2005

(54) METHOD AND APPARATUS FOR IMPROVED INSPECTION AND CLASSIFICATION OF ATTRIBUTES OF A WORKPIECE

(75) Inventors: Steve C. Woods, Salmon Arm (CA);
Michael McGuire, Salmon Arm (CA);
Harry Ogloff, Salmon Arm (CA);
Zvonimir Skočić, Salmon Arm (CA);
Emeric Johnson, Salmon Arm (CA)

(73) Assignee: Coe Newnes/McGehee ULC, Salmon Arm (CA)

( * ) Notice: Subject to any disclaimer, the term of this patent is extended or adjusted under 35 U.S.C. 154(b) by 0 days.

(21) Appl. No.: 10/610,426

(22) Filed: Jun. 30, 2003

(65) Prior Publication Data

US 2004/0030536 A1 Feb. 12, 2004

Related U.S. Application Data

(62) Division of application No. 09/900,095, filed on Jul. 5, 2001, now Pat. No. 6,594,590, which is a division of application No. 09/061,723, filed on Apr. 17, 1998, now Pat. No. 6,272,437.

(51) Int. Cl.[7] .............................................. G06F 19/00
(52) U.S. Cl. .......................... 702/189; 700/700; 700/2; 700/9; 719/328; 709/203
(58) Field of Search ............................. 702/189; 700/1, 700/2, 9; 719/328; 718/100, 101, 102, 103, 107; 709/203

(56) References Cited

U.S. PATENT DOCUMENTS 5,802,263 A * 9/1998 Dittmar et al. ................. 714/4
6,266,138 B1 * 7/2001 Keshavmurthy ......... 356/237.2
6,272,437 B1 * 8/2001 Woods et al. .................. 702/35
6,594,590 B2 * 7/2003 Woods et al. .................. 702/35
6,748,455 B1 * 6/2004 Hinson et al. .............. 719/318
2004/0015833 A1 * 1/2004 Dellarocas et al. ......... 717/106

OTHER PUBLICATIONS

Di Stefano et al., "Synchronous Producer–Consumer Transactions for Real–Time Distributed Process Control", IEEE, 1997.*

* cited by examiner

Primary Examiner—Patrick J. Assouad
(74) Attorney, Agent, or Firm—Antony C. Edwards

(57) ABSTRACT

A generic, scalable consumer subsystem/producer subsystem interface controller for exchanging data between at least one producer subsystem configured to produce a set of services characterized in a producer generated data set, and at least on consumer subsystem configured to consume the set of services, including an object-oriented producer application program interface configured for use on a multi-threaded, client-server operating system, wherein producer routines are configured to: initialize producer server objects maid producer client objects; receive requests for data from a consumer subsystem via the producer client objects; send acknowledgments to a consumer subsystem in response to requests from the consumer subsystem via the producer server objects; send data to a consumer subsystem in response to requests from the consumer subsystem via the producer server objects; and wherein consumer routines are configured to: initialize consumer server objects and consumer client objects; send requests for data to a producer subsystem via the consumer server objects; receive acknowledgments from a producer subsystem in response to requests from the producer subsystem via the consumer client objects; and, receive data from a producer subsystem in response to requests from the producer subsystem via the consumer client objects.

6 Claims, 11 Drawing Sheets

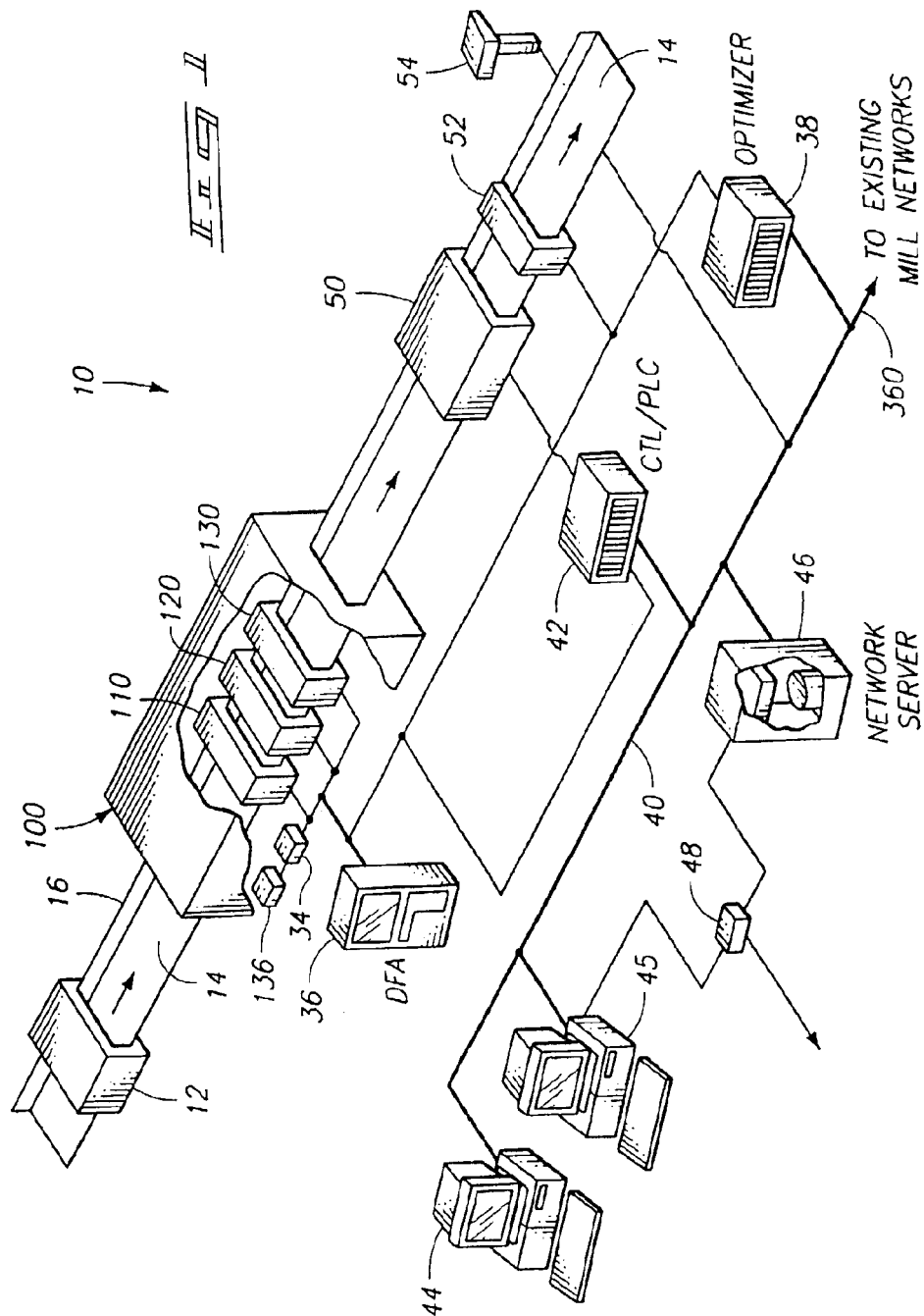

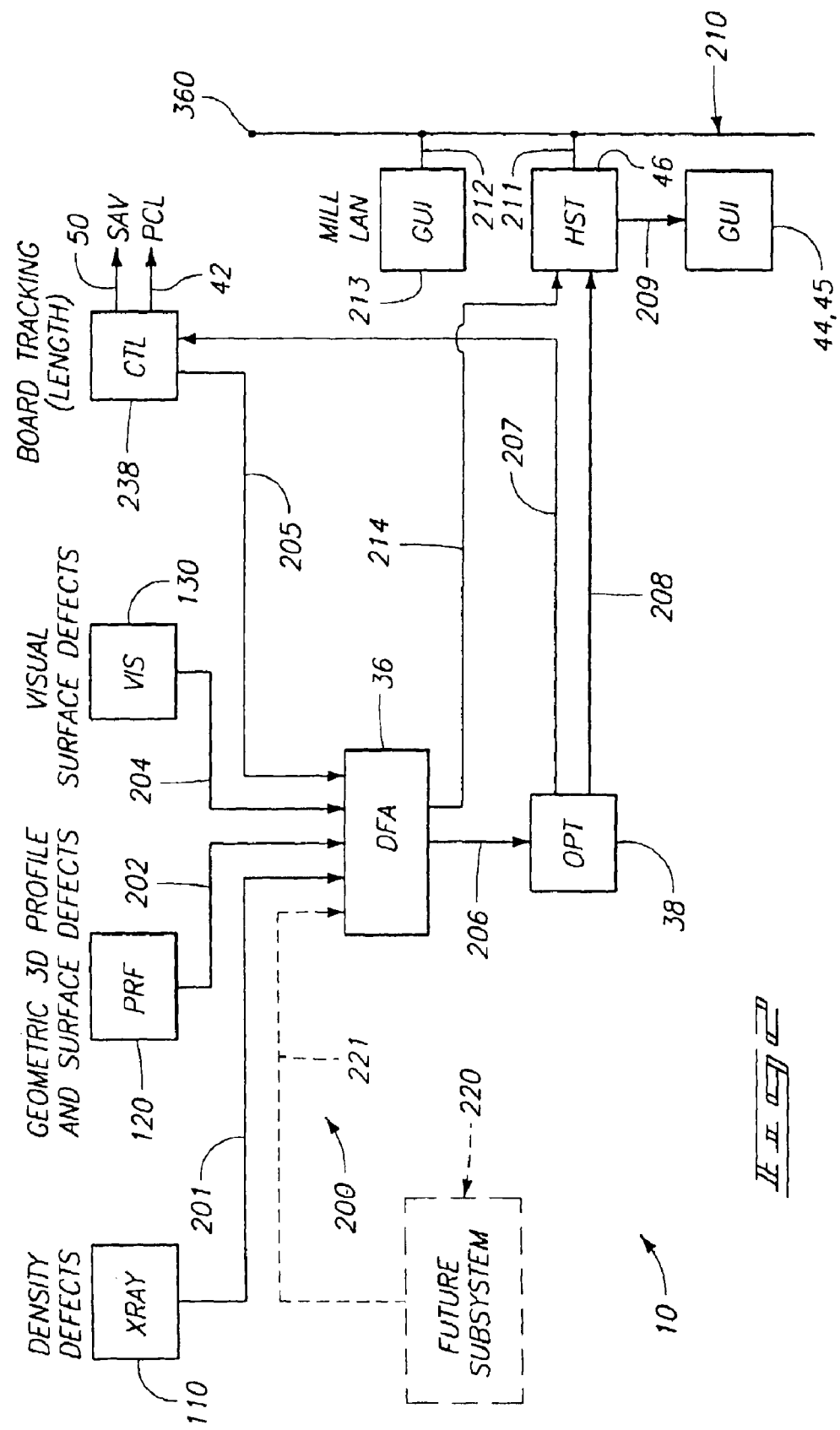

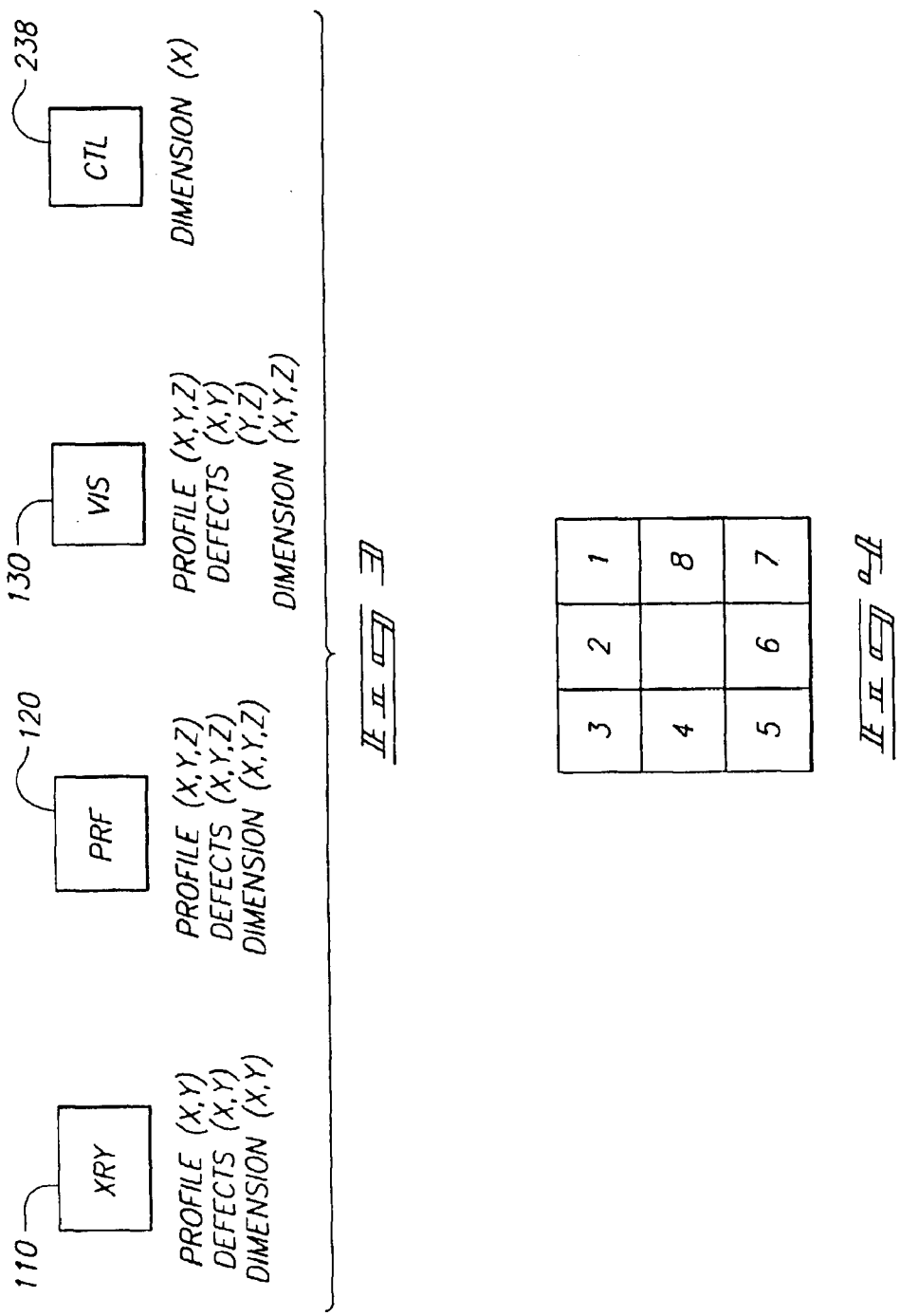

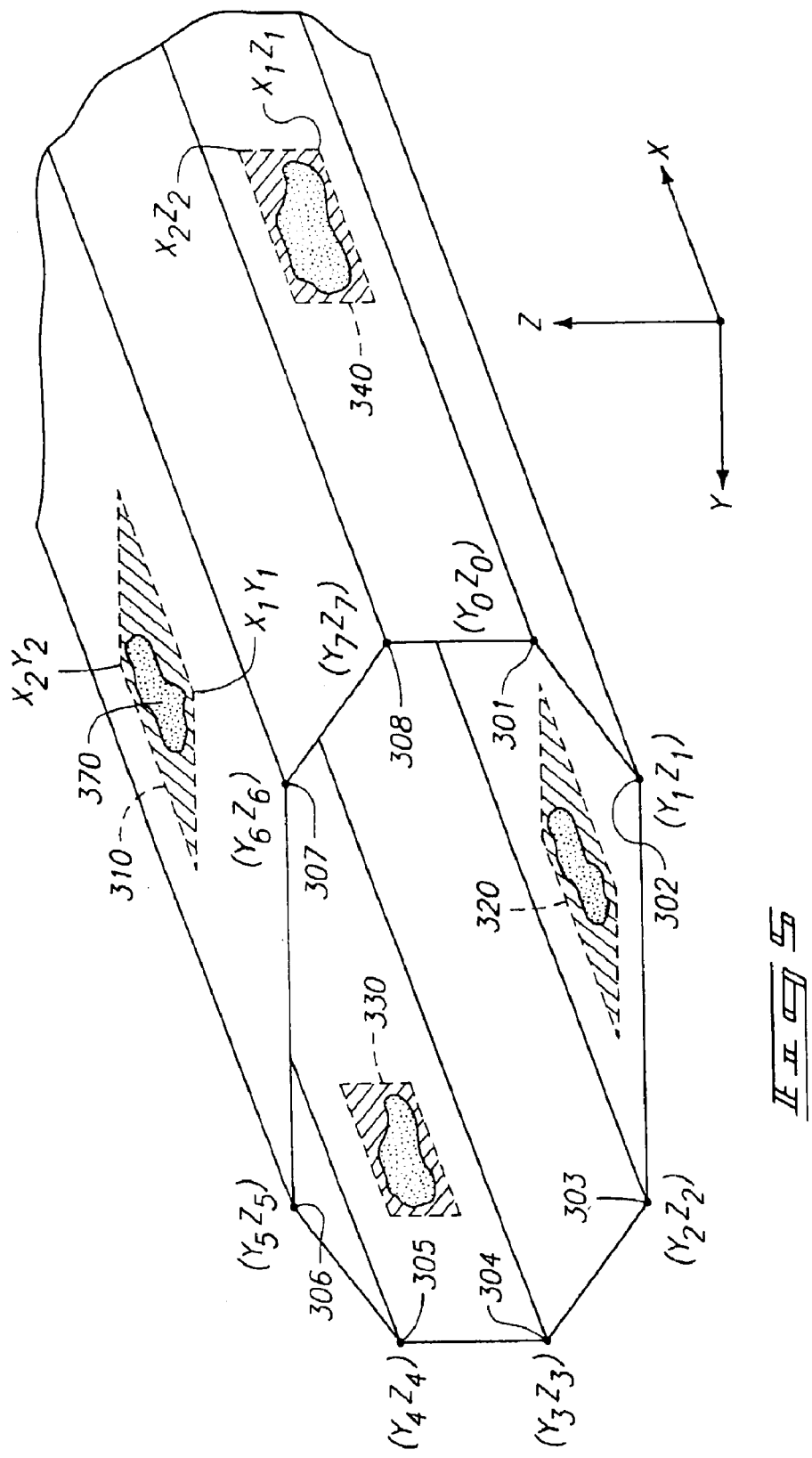

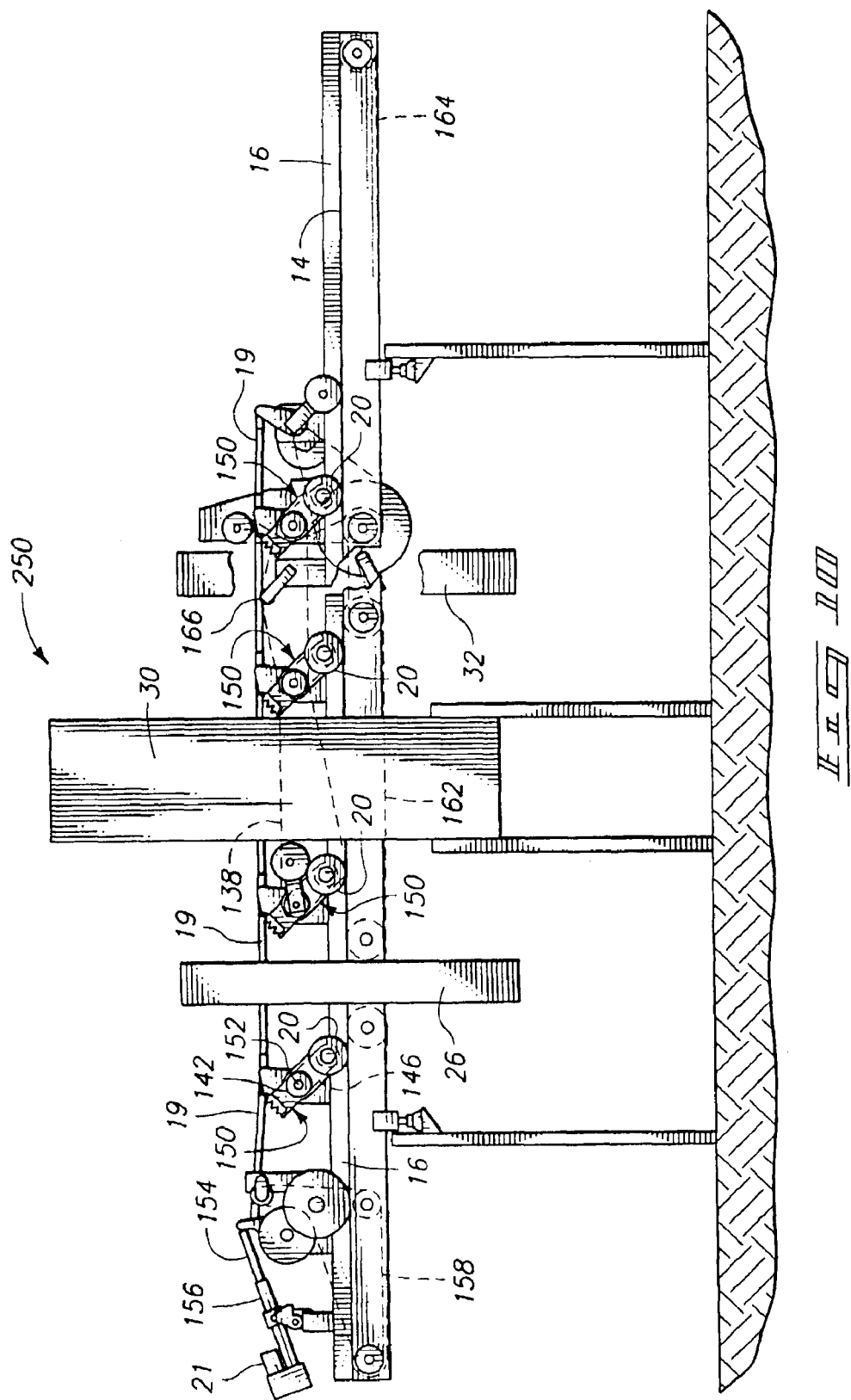

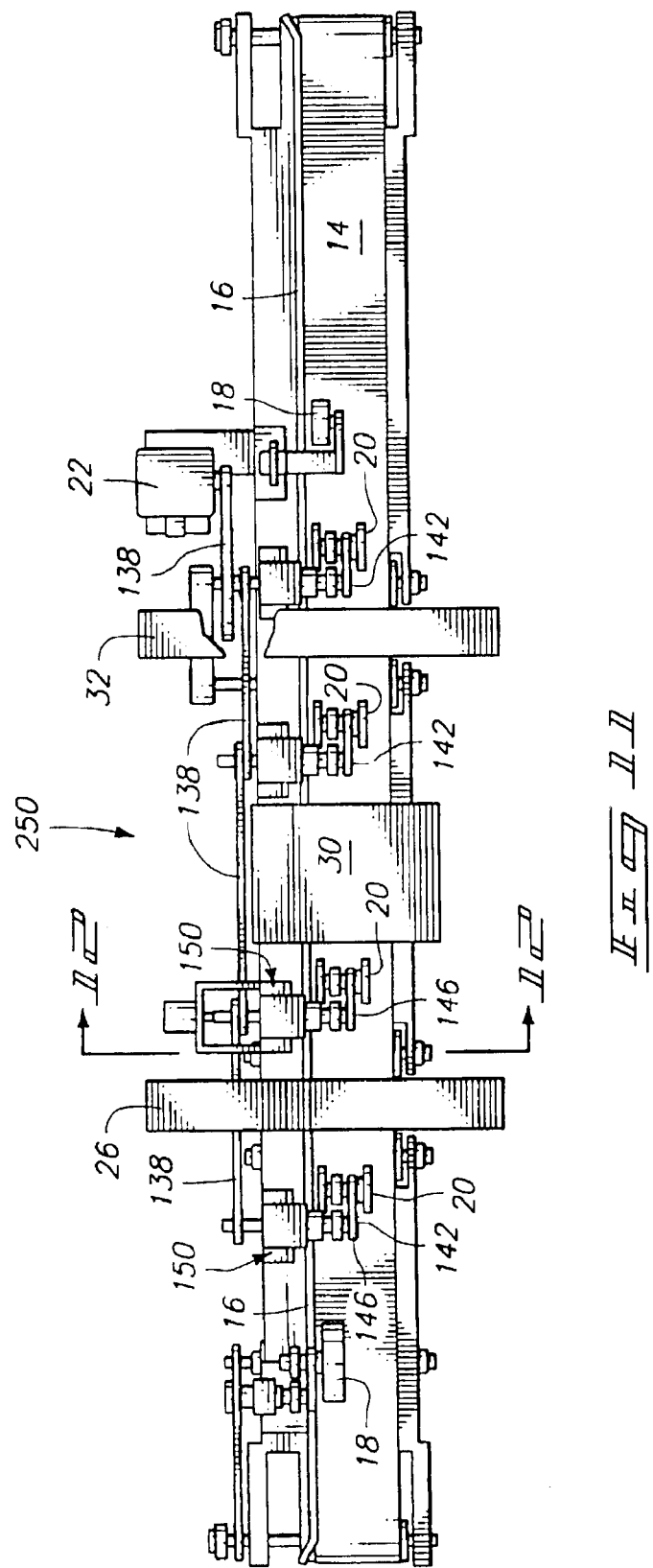

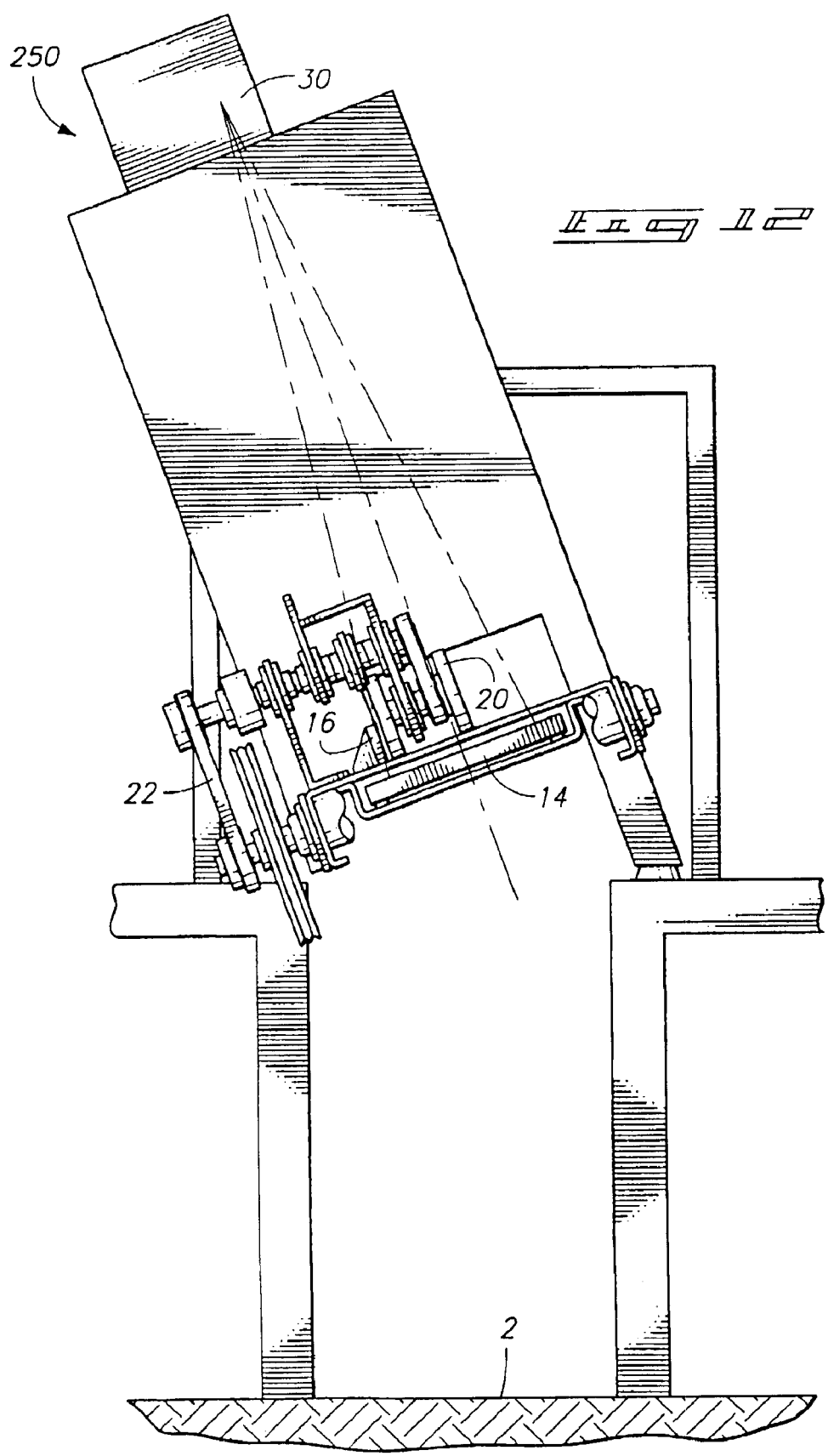

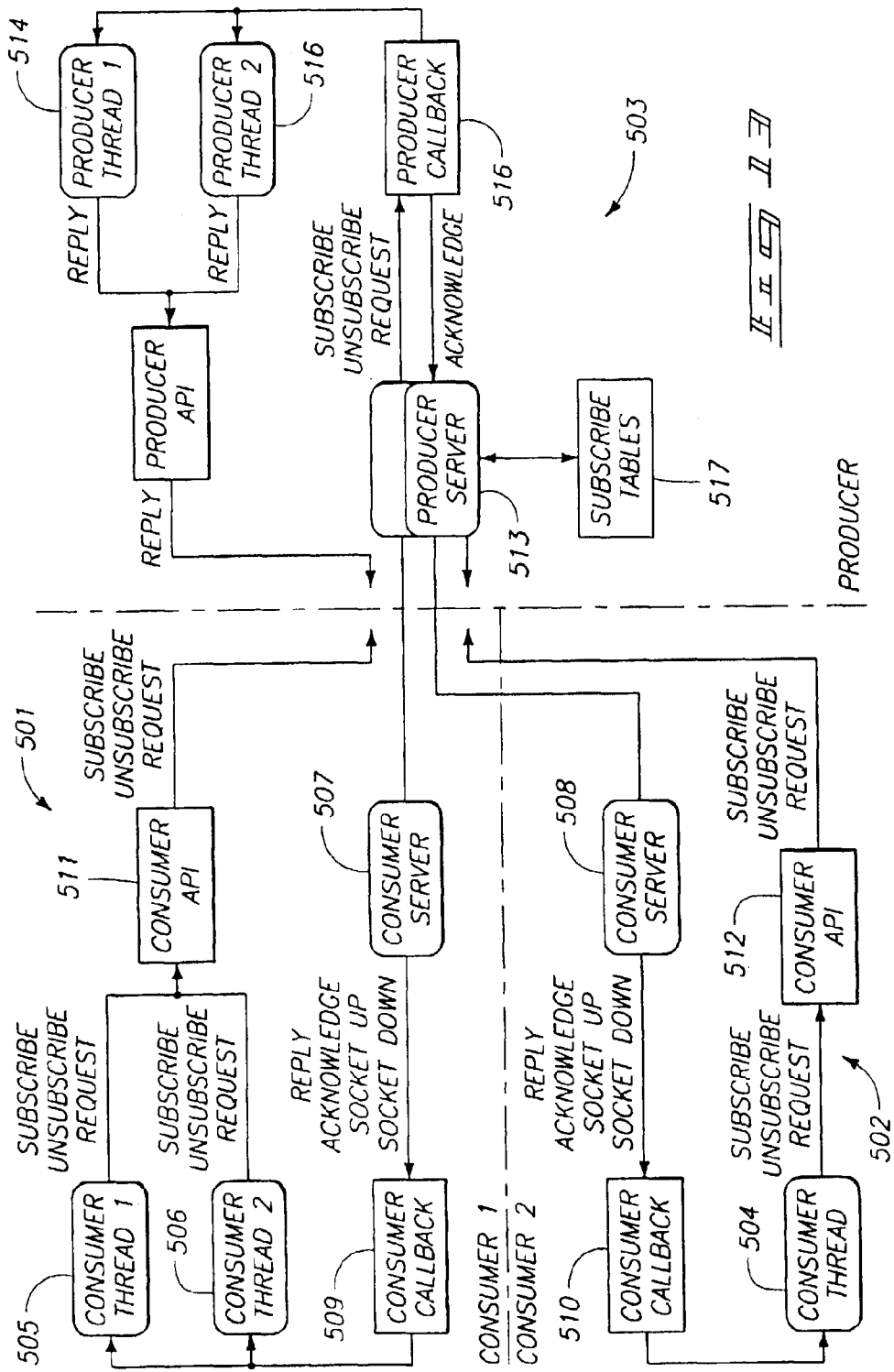

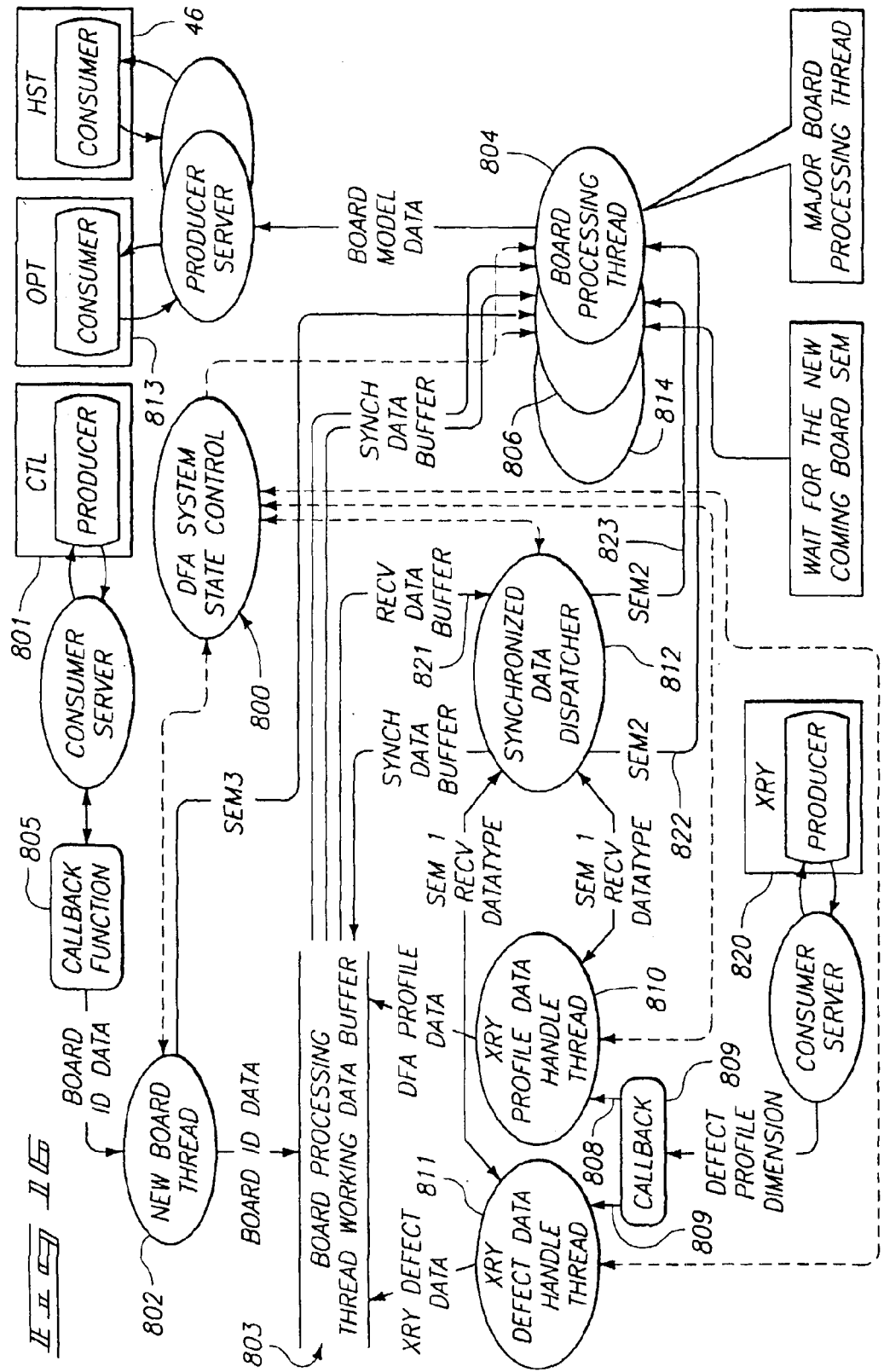

METHOD AND APPARATUS FOR IMPROVED INSPECTION AND CLASSIFICATION OF ATTRIBUTES OF A WORKPIECE

CROSS REFERENCE TO RELATED APPLICATIONS

This application is a divisional of U.S patent application Ser. No. 09/900,095 filed Jul. 5, 2001 and entitled "Method and Apparatus For Improved Inspection and Classification of Attributes of a Workpiece," now U.S. Pat. No. 6,594,590, which in turn division of U.S. patent application Ser. No. 09/061,723 filed Apr. 17, 1998 and entitled "Method and Apparatus For Improved Inspection and Classification of Attributes of a Workpiece," now U.S. Pat. No. 6,272,437.

FIELD OF THE INVENTION

This invention relates to a method and apparatus for improved inspection and classification of attributes of a workpiece, and in particular to automated high speed defect assembly and generation of a workpiece model for lumber grading.

BACKGROUND OF THE INVENTION

It has become a serious consideration in the lumber industry to improve grading of lumber and therefore improve secondary breakdown decisions. By optimizing the recovery of "good wood" against a slate of desired products, the value of the lumber may be increased. "Good wood" refers to wood which meets a prescribed criteria. For different uses, what is considered "good wood" may vary. For example, for fine furniture, it may not be acceptable to have any knots in the wood. However, for furniture intended to have a more rustic appearance, a certain number of knots may in fact be desirable. In general though it is desirable to identify certain "defects" in the lumber, and to locate them with respect to a spatial reference system. One method of doing this is to have a human visually inspect each piece of lumber prior to it being cut into secondary boards. This is slow and prone to error. Further, even if the defect is identified, the information must still somehow be communicated to a saw operator in a meaningful manner to allow the defect to be isolated, yet allow wood recovery to be optimized against a desired product slate.

There have been some improvements in the area of grading lumber, for example Lumber Optimizer (U.S. Pat. No. 4,879,753 to Aune et al), Method of Estimating the Strength of Wood (U.S. Pat. No. 4,941,357 to Schajer), Dielectric Sensor Apparatus (U.S. Pat. No. 5,654,643 to Bechtel et al), Detector for Heterogeneous Materials (U.S. Pat. No. 5,585,732 to Steele et al), and Flaw Detection System Using Microwaves (U.S. Pat. No. 4,514,680 to Heikkilä et al) which uses microwaves to measure lumber flaws.

Defects comprise such features as knots, rot, splits, sap, skips, holes, cracks, wane, stain and the like. Defects may be further subclassified, for example a knot may be a sound knot or an unsound knot. Most defects have some attribute which allows them to be detected by automated scanning. For example, reflective inspection (laser or gray-scale video) can detect stain and sap in wood. Transmissive inspection techniques (such as x-ray) can detect density variations, and thus knots and rot and the like. As indicated, a variety of automatic inspection techniques exist for determining the presence of such defects. Most of these methods give only an indication of the probability of a defect, and do not guarantee that the object identified by the inspection technique is actually a defect. However, by combining the different results of automatic inspection into a single model, defects can be verified and the probability that an identified object is in fact a defect are increased. Further, combining inspection results allows further characterization of a defect. For example, a dark area identified by a visual scan can either indicate rot, stain, or a knot. However, verification of the visual scan with an x-ray scan can reveal the object to be rot if the x-ray scan indicates it is an area of low density, or a knot if the x-ray scan indicates it is an area of high density.

It is desirable if all of the results of inspection can be combined to produce a board model, which in the digital realm might be more appropriately termed a "virtual board." The board model can then be analyzed for optimum yield against a product slate. Further, automated handling machines such as conveyors, and automated process machines such as saws, can control the handling and processing of the physical board on which the board model is based.

It is further desirable to have a system which is flexible and can easily accommodate the addition or subtraction of additional components, such as additional inspection subsystems, user interfaces, computer controlled machines (saws, etc.), and additional technology as it becomes available.

For any such system to be effective, it is desirable that the system be able to determine the precise location of the board at various points throughout the system. Various prior art tracking systems such encoder wheels can become inaccurate due to slippage, and can cause undesirable marking of the product in the event of a failure. It is therefore desirable to provide a tracking system which is accurate and reliable.

SUMMARY OF THE INVENTION

An apparatus for detecting the probable existence, location, and type of defects in a workpiece is disclosed. The apparatus has a signal processor having a computer readable memory, a control subsystem, and a sensor subsystem. The sensor subsystem is configured to sense a first section of the workpiece and produce signals corresponding to at least one physical characteristic of the section of the workpiece and store the signals in the computer readable memory. The processor is configured to read the signals from the computer readable memory, to verify the signals, to generate defect types by comparing the signals to a rule set, and to generate a data model of the workpiece section. The control system is configured to generate a workpiece section identifier to specifically identify a workpiece section being sensed and provide the workpiece section identifier to the processor. The processor is further configured to receive the signals for the first workpiece section to a first workpiece processing thread after receiving the associated workpiece section identifier, and to generate a second workpiece processing thread for receiving signals from a second workpiece section. The signals in the first workpiece processing thread are processed to generate the data model of the first workpiece section prior to processing of the signals in the second workpiece processing thread.

The invention further includes an apparatus for detecting the probable existence, location, and type of defects in a workpiece wherein the apparatus includes a sensor subsystem as described above, a defect assembler, an optimizer, and a computer system. The defect assembler is configured to generate defect assembler data, subscription requests, to receive the signals produced by the sensor subsystem, and to generate a workpiece data model based on the signals. The optimizer is configured to generate workpiece segmentation recommendations based on the workpiece data model, and generate optimizer data subscription requests. The computer system further includes a processor and a computer readable memory. The computer system is configured to receive signals form the sensor subsystem and store them in the computer readable memory. The processor is configured with a first producer thread program which, in response to the receipt of a first set of signals by the computer system, receives one of the data subscription requests and transmits the first set of signals from the computer readable memory to the generator of the data subscription request. The processor is further configured to generate a second producer thread in response to a storage of a second set of signals in the computer readable memory, the second producer thread being configured to receive one of the data subscription requests and selectively send the second set of signals to the generator of the data subscription request.

The invention further includes an apparatus for characterizing a workpiece, the apparatus including an interface controller, a plurality of producer units, and a plurality of consumer units. The producer units are configured to produce data relevant to characterization of the workpiece. The producer units are selected from the group consisting of sensor subsystems, a defect assembler, an optimizer, and a data controller. The sensor subsystems are configured to sense features of the workpiece and generate signals in response thereto. The defect assembler is configured to generate a workpiece data model. The optimizer is configured to produce a refined workpiece data model and generate workpiece segmentation recommendations based on the refined workpiece data model. The controller is configured to determine the position of the workpiece during sensing and segmentation. The producer units are configured to notify the interface controller the workpiece data is available from the producer unit. The consumer units are configured to use data relevant to characterization of the workpiece. The consumer units are selected from the group consisting of an optimizer, a defect assembler, a host computer, and user interfaces. The optimizer is configured to use the refined workpiece model to generate workpiece segmentation recommendations. The defect assembler is configured to use signals from the sensor subsystems to generate the workpiece data model. The host computer is configured to store workpiece characterization data. The user interfaces are configured to display workpiece characterization data. Workpiece characterization data are selected from the group consisting of signals from the sensor subsystems, the workpiece data model, and the refined workpiece data model. The consumer units subscribed to selected workpiece characterization data. The interface controller includes a processor configured to generate producer threads to respond to workpiece characterization data subscriptions from the consumer units in response to notification from the producer units the workpiece data is available from the producer unit. The processor is further configured to send workpiece characterization data to selected consumer units in response to workpiece characterization data subscriptions from the selected consumer units.

The invention also includes a method for generating a workpiece model comprising the steps of:

reading signals from a computer readable memory, the signals being representative of at least one physical characteristic of a first section of a workpiece;

reading a first workpiece section identifier from the computer readable memory, wherein the first workpiece section identifier specifically identifies the first workpiece section associated with the signals;

associating the signals for the first workpiece section to a first workpiece processing thread after receiving the associated workpiece section identifier;

generating a second workpiece processing thread for receiving signals from a second workpiece section; and prior to the processing of the signals in the second workpiece processing thread, processing the signals in the first workpiece processing thread that generated the data model of the first workpiece section.

The invention further includes a computer readable medium having computer executable instructions for performing the steps of the above-described method.

The invention further includes a workpiece characterization system including at least one producer subsystem configured to produce a set of services relating to physical characteristics of a workpiece, at least one consumer subsystem configured to consume the set of services, and an interface controller for exchanging data between the subsystems in a generic, scalable manner. The interface controller includes an object-oriented producer application program interface (API) and an object-oriented consumer API. The APIs are configured for use on a multi-threaded, client-server operating system. The producer API is configured to initialize producer server objects and producer client objects, to receive requests for data from a consumer subsystem via the producer client objects, to send acknowledgments to a consumer subsystem in response to requests from the consumer subsystem via the producer server objects, and to send data to a consumer subsystem in response to requests from the consumer subsystem via the producer server objects. The consumer API is configured to initialize the consumer server objects and consumer client objects, to send requests for data to a producer subsystem via the consumer server objects, to receive acknowledgments from a producer subsystem in response to requests from the producer subsystem via the consumer client objects, and to receive data from a producer subsystem in response to requests from the producer subsystem via the consumer client objects.

The invention further includes an apparatus for tracking select kinematics of a workpiece moving at a linear velocity. The tracking apparatus includes an encoder wheel, a drive mechanism, and a signal generator. The encoder wheel is configured to tangentially contact a workpiece and rotate at an angular velocity coincident with the linear velocity of the workpiece in response to contact between the encoder wheel and the workpiece. The drive mechanism is configured to drive the encoder wheel at a first angular velocity approaching an angular velocity of the encoder wheel coincident with the linear velocity of the workpiece. The signal generator is configured to interact with the encoder wheel and generate a signal in response to the angular velocity of the encoder wheel.

The invention further includes an apparatus for detecting the probable existence, location, and type of defects in a workpiece. The apparatus includes a sensor subsystem, a defect assembler, an optimizer, a computer controllable workpiece segmenter, a control subsystem, a computer system, and a tracking device. The sensor subsystem is configured to sense a first section of a workpiece and produce signals corresponding to at least one physical characteristic of the section of the workpiece. The defect assembler is configured to generate defect assembler data subscription requests, to receive the signals, and to generate a workpiece data model based on the signals. The optimizer is configured to generate workpiece segmentation recommendations based on the workpiece data model and generate optimizer data subscription requests. The computer controllable workpiece segmenter is configured to segment a workpiece according to the segmentation recommendations. The control subsystem is configured to control the workpiece segmenter in response to the location of a workpiece within the apparatus and in response to the workpiece data model and the segmentation recommendations. The computer system includes a processor and computer readable memory. The computer system is configured to receive signals from the sensor subsystem and store them in the computer readable memory. The processor is configured with a first producer thread program which, in response to the receipt of a first set of signals by the computer system, receives one of the data subscription requests and transmits the first set of signals from the computer readable memory to the generator of the data subscription request. The processor is further configured to generate a second producer thread in response to storage of a second set of signals in the computer readable memory, the second producer thread being configured to receive one of the data subscription requests and selectively send the second set of signals to the generator of the data subscription request. The tracking device is configured to track selected kinematics of a workpiece moving in a linear velocity within the apparatus. The tracking device includes an encoder wheel, a drive mechanism, and a signal generator. The encoder wheel is configured to tangentially contact a workpiece and rotate at an angular velocity coincident with the linear velocity of the workpiece in response to contact between the encoder wheel and the workpiece. The drive mechanism is configured to drive the encoder wheel at a first angular velocity approaching an angular velocity of the encoder wheel coincident with the linear velocity of the workpiece. The signal generator is configured to interact with the encoder wheel and generate a signal in response to the angular velocity of the encoder wheel and provide the signal to the control subsystem.

The invention provides other advantages which will be made clear in the description of the preferred embodiments.

BRIEF DESCRIPTION OF THE DRAWINGS

The invention will be better understood by reference to drawings, wherein:

FIG. 1 is an isometric schematic diagram showing a modern lumber mill and the system for determining the presence of defects in a board and making optimization decisions based thereon.

FIG. 2 is a schematic diagram showing the interrelation between the various components of the system in a block diagram format.

FIG. 3 is table showing the different attributes of a workpiece such as a board which can be sensed by various sensing or measuring subsystems.

FIG. 4 is an end view of a workpiece such as a board showing the 9 segments that the board may be divided into for purposes of producing a board model.

FIG. 5 is an isometric diagram of a visual representation of a board model or "virtual board".

FIG. 10 is a side elevation view of a board tracking device.

FIG. 12 is an end view of the board tracking device of FIG. 10.

FIG. 13 is a schematic diagram of a model of the type of message used in the interface control subsystem.

FIG. 14 is a diagram of a four-point defect bounding box for external bounding and secondary internal feature bounding.

FIG. 15 is another diagram of a four-point defect bounding box for external bounding and secondary internal feature bounding.

FIG. 16 is a schematic diagram of the defect assembler architecture.

DETAILED DESCRIPTION OF EMBODIMENTS OF THE INVENTION

Figure 8:
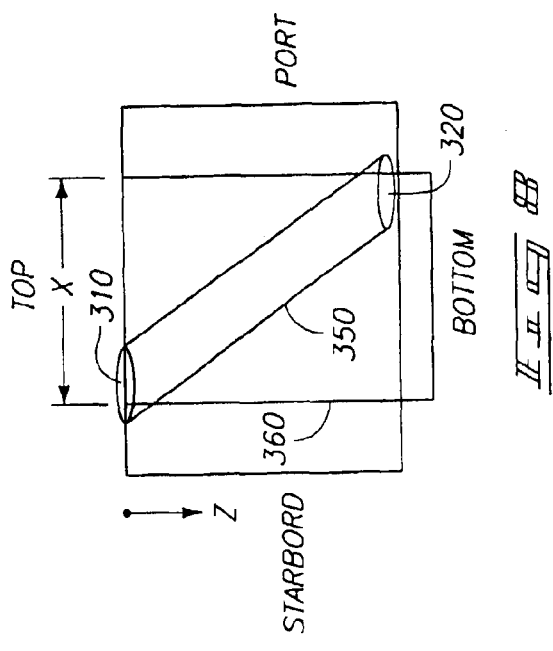
FIG. 8 is an end elevation view of a section of a board having a knot passing therethrough.

Referring to FIG. 1, the system 10 is made up of a number of modules or subsystems which beneficially work together to scan each board and produce an optimized decision. These subsystems detect board features and defects, optimize the board, and preferably pass the optimized decision for each board to the appropriate saw.

The sensing subsystem 100 can include x-ray 110, profile 120, laser profile (not shown), color vision 130, fluorescent mark reader (not shown), moisture (not shown), and inspection and sensing systems (not shown). The optimizing subsystems include the defect assembler 36, scheduler (not shown), and the optimizer and control subsystems 38, 42 and 138 of FIG. 2. These subsystems get their operational instructions such as product definitions, prices, etc., from a database maintained by the host subsystem 46 and accessed by the graphical user interfaces 44 and 45.

When a board enters the system 10 it is detected by a barrier photoeye 34 and can be tracked using an electronic encoder 136. Images of the board are collected from the various sensors 110, 120 and 130 one "slice" (data slice) at a time as the board travels through the scanner 100. When a number of "slices" have been acquired this is termed a "frame" of data. Frames can then be evaluated for the features and defects that the sensors identify as likely to exist in the board.

As each frame is evaluated the features and defects are passed from the sensing subsystems 100 to the defect assembler 36. The defect assembler 36 adds all of the defect and feature information together from the various sensing subsystems and passes the board model on to the optimizer 38.

The optimizer 38 evaluates the board for the products defined in the current cut order and generates an optimum decision. This decision may include fixed length products, finger joint (variable length) products, and re-rip products. It can place the products towards the leading end of the board, the trailing end of the board, or centered in the board between defects. The decision will be based on either recovery optimization (get the most wood possible out of the board) or on value (get the most money possible out of the board). Each product can be defined to allow or not allow certain defects in certain parts of the product cross section. This means that products that will be machined further can allow defects in the product where the defect will be removed at a later step in the process. This decision is preferable complete by the time that the board exits the scanner 100 and is in turn displayed on the graphical user interface 44 or 45 (real-time display) and is passed on to the control subsystem 138 of FIG. 2.

The control subsystem 138 tracks the board through the system by assigning it an identification number which all of the other subsystems use to make sure that they are referencing the same board. Once a board decision has been made the control subsystem communicates with a material handling process controller (not shown and not part of the system) to determine which saw the cut decision is to be sent to. At the appropriate time, the cut decision (including positions along the board at which to cut, and which storage bin the resulting block of wood is to be sent to) is then transmitted directly to the computer controlled saw 50. A plurality of saws can be fed simultaneously by one system.

As each board passes through the system 10 and a decision is made, the board data and decision are stored in a database in computer 46. Production summary reports can be generated from this data providing users with a clear picture of what product volumes were produced. Each board's information may also be saved in a manner that allows it to be re-optimized later during a "what-if" system tuning exercise. This is an effective way to tune the system without the time and cost of processing real wood.

In addition to using the board model generated by the system for purposes of optimizing board segmentation and for controlling the execution of board segmentation by saws and the like, the board model can be saved on a computer readable medium for future use. For example, rather than segmenting the boards associated with a saved board model, the physical boards might be sold to a customer for further processing along with an accompanying copy of the board model on computer readable medium. This will allow the buyer to make local decisions regarding segmenting the boards, and can also allow the buyer to perform such segmentation of the board with machines capable of using the board model for machine positional control. Likewise, a potential buyer of boards can preview the boards by viewing the board model to determine whether the boards meet the buyers needs.

Overview of the System

FIG. 1 shows an overview of the system 10 for grading and handling graded lumber, including the cutting of boards, which is generally found in a sawmill. Lumber or a workpiece 1 generally advances into the plant from a planer 12 on a feed belt 14 adjacent a fence 16.

The system 10 is preferably provided with sensors to allow the tracking a detection of workpieces as they move through the system. Workpieces may be marked with bar code by bar coder 52, allowing the board to be tracked as it moves through the plant or identified in a package of boards for later distribution or use. For workpieces such as lumber where it can be undesirable to visibly mark boards, bar coding may be accomplished by using ink which can only be read by non-visible light frequencies (such as ultraviolet).

It is also desirable to know, at various points in the system, the precise location of a board. Such is particularly useful after a board has been optimized to identify defects and then presented to a saw for the cutting. Without precise location identification of the board, defects may be left in the board, or alternately, good wood cut out of the board. Preferred apparatus for such tracking of boards in a computerized optimization sawmill are described herein.

Turning to FIG. 2, a hierarchal block diagram is provided showing the relationship between the subsystem components. The system 10 includes sensing or inspection subsystem shown as x-ray 110, profile 120, and visual 130. The x-ray inspection subsystem can determine density defects and shuttle profile of the workpiece. The profile sensing subsystem can determine a geometric 3-dimensional profile of the board or workpiece, as well as the existence of surface defects. The visual inspection subsystem can determine visual surface defects. As described above, other sensing and inspection subsystems can be added to the system. The particular system provided makes it easy to add additional inspection subsystems as will be described further below. The system 10 further comprises a board tracking subsystem 138 which, in addition to tracking the position of the board within the plant as well as the position of the board within subsystems such as the sensing subsystems, can determine the length of the board. The control subsystem 138 further communicates with a computer controlled saw 50 of FIG. 1 as well as the programmable logic controller or PLC 42 of FIG. 1. The sensing subsystems as well as the control subsystem communicate directly with the defect assembler 36. As described above, the defect assembler generates a board model or a "virtual board." The defect assembler is in communication with the optimizer 38. The optimizer 38 is in communication with the controller 138 such that the optimized decisions made by the optimizer 38 can be communicated to the controller 138 allowing the controller to execute the decisions. The optimizer 38 is in further communication with the host 46 allowing the optimizer 38 to access and store data, including computer programs, on the computer readable medium of the host. In traditional network architecture, the host supports user interfaces such as terminals 44 and 45. The host may be in further communication with a main bus line to 40 which can support additional user interfaces such as operator console 54 of FIG. 1 or user interface 213 of FIG. 2, as well as communicate with the existing mill networks by node 360.

Connecting all of the subsystems is the interface controller (IFC) 200 of FIG. 2. The interface controller 200 consists of communication links 201, 202, 204 through 212, inclusive, and 214. The interface controller 200 is further configured such that future subsystems 220 can be added and accommodated through communication channel 221. Likewise, components such as user interface 213 may be removed and communication channel 212 removed without difficulty, due to the structure of the interface controller as will be further described below. The system 200 can further beneficially include a communication link 214 between the defect assembler and the host allowing the defect assembler to store the board model on the computer readable medium of the host 46.

It is understood that, while the system of the present invention is primarily described as having a plurality of sensor subsystems, the system can comprise only a single sensor subsystem. An example of single sensor subsystem use is in a primary breakdown operation wherein large pieces of wood (as for example, logs) are cut into primary bulk pieces for latter processing into smaller, commercial sized pieces. A primary breakdown operation can be performed using only a profile sensor to determine wane or a "no-board" condition. The resulting information can then be provided to the optimizer and the controller for cutting of the log into primary components. In such case the interface controller cans still be used to integrate the optimizer and the optimizer.

Turning to FIG. 3 a block diagram table is provided showing a variety of sensing subsystems and the types of data that they produce. Board data may be generally separated into three different categories. The first category is a profile data set which provides information about the physical dimensions of the board in 1, 2, or 3 dimensions (represented by Cartesian coordinates x, y and z). The next category is defect information which may either be 2-dimensional or 3-dimensional. For example, a single source x-ray system can provide 2-dimensional defect information, particularly relating to density variations in the work piece. A profile subsystem can provide defect information in 3-dimensions, but is limited to detecting such defects as gouges, holes, and other defects which affect the profile of the board itself. A third category is a dimensional category. Again, different subsystems can provide different dimensional information. For example, the x-ray subsystem can provide dimensional information relating to the width and length (x and y) of the board while the control system can only provide information relating to the length of the board.

In FIG. 3, each of the three categories are shown with respect to four sensing subsystems 110, 120, 130 and 238, and each category is further defined with respect to the number of dimensions (referenced by coordinates x, y and z) in which the category can be measured for each of the shown subsystems.

The information collected from the subsystem shown in FIG. 3 is used to build a board model. Turning to FIG. 4, an end view of a workpiece or board is shown. For modeling purposes, it is convenient to segment the board into eight segments. Assuming that FIG. 4 shows the end of a board which leads travel through the system, segments 1, 2 and 3 border the top of the board, while segments 5, 6 and 7 border the bottom of the board. Likewise, segments 1, 8 and 7 border the port side of the board (referenced by looking at the top facing towards the leading edge), while segments 3, 4 and 5 border the starboard side of the board. It is convenient to segment the board into eight of segments since such segmentation conveys the Wandefelt information relevant to board characterization.

Turning to FIG. 5, an isometric visual diagram of a board model or "virtual board" is shown. The board model is preferably constructed using 8 vertices 301 through 308. Eight vertices are selected since most physical board shapes may be accommodated with an 8-point model. Briefly referring to FIG. 6, it is seen that when a perfectly rectangular board is encountered that the corner vertices will collapse, as exemplified by vertices 301 and 308.

Figure 7:
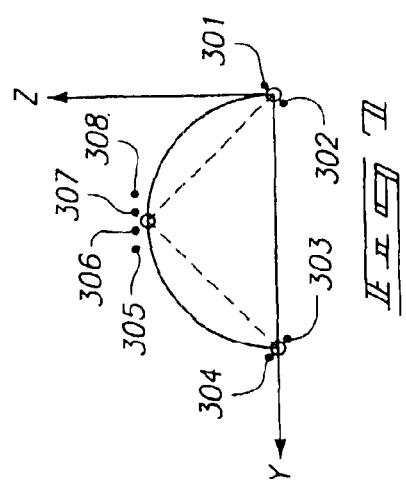
FIG. 7 is an end view diagram of the board model of FIG. 5 wherein the corner vertices and the top vertices collapse for a board exhibiting severe wane.

Briefly turning to FIG. 7, it is further seen that for a board such as a piece of wood cut near the edge of a tree exhibiting significant roundness on one side, the vertices will collapse even further as shown by vertices group 302, 303, 304 and 305.

Returning now to FIG. 5, a Cartesian coordinate system having coordinates of x, y and z corresponding respectively to the length, width, and height of the virtual board is shown. Such a reference system is useful for generating, storing, and manipulating a computer model such as the virtual board described herein.

Figure 9:
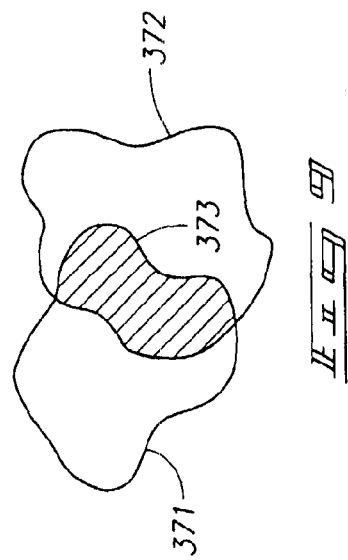
FIG. 9 is a plan view of a defect map showing a defect sensed by two different sensing subsystems, and how the defects might be merged into a single defect.

The virtual board of FIG. 5 is further shown with defects 310 on the top side, 320 on the bottom side, 330 on the port side, and 340 on the starboard side. It is the job of the defect assembler to take this information and assemble it into a board model to generate a model which is representative of the physical board. For example, a visual scanner may determine only that defect 310 and defect 320 exist on the top and bottom respectively of the actual board. However, there is no data which connects these two together so it is impossible for a visual scanning subsystem to determine whether there is any relationship between the two defects. If the defect is a knot which passes through the board at an angle, as shown in FIG. 8 showing knot 350 having top 310 and bottom 320, an x-ray scanner will only determine that a defect of width x exists in the board, since it will not have any information regarding the location of the defect with respect to the depth of the board. The defect assembler can take both the visual information showing defects 310 and 320, as well as the x-ray information showing a block defect 360, and combine them together to determine that in fact the defect is a knot which passes through the board. This type of data combining is shown graphically in FIG. 9 wherein an x-ray defect 371 is combined with a visual defect 372 producing an overlapping defect zone 373. It is the function of the defect assembler to compare this information against other acquired information and determine the probable existence, type, and location of a real defect within the board and generate an appropriate board model in response thereto.

The defect assembler as well as the other components and subsystems of the system, will be described more fully below.

Subsystems

Inspection and Sensing Subsystems

X-Ray

The x-ray subsystem 110 of FIG. 1 transmits x-rays through lumber as it travels lengthwise through the scanner 100. The x-rays are blocked according to the density of the wood at given locations which results in greater attenuation of x-rays at the detectors when there is high density wood present such as knots, and less attenuation of x-rays when there is lower density such as clear wood, and even less attenuation when there is extremely low density in the cases of rot. By evaluating the x-rays that are received, the system can locate knots, rot, and clear wood. This information is summarized by the system and preferably passed on to the defect assembler 36.

Vision

The vision subsystem 130 illuminates a board with white light which is reflected into a color linescan camera. The amount and color of the reflected light varies according to the type of wood traveling through the scanner and the features or defects at a particular location on the board. Using this color visual information the system can locate the surface locations of knots, cracks, holes, stains, insect damage, etc. A number of techniques are used in evaluating the image to locate these features which are then summarized and preferably passed on to the defect assembler 36.

Profile

The profile subsystem 120 illuminates the sides of a board with white light which is then reflected to cameras above and below the board faces. The amount of light reflected from the edge depends on the slope of the board edge. In this way, the system determines the presence and width of wane along the board edges. This information is summarized and preferably passed on to the defect assembler 36.

Laser Profile

A laser profile subsystem (not shown) projects lines of laser light onto a board at an angle. The light is reflected to a camera looking at the board from a different angle. The difference in projection and viewing angles of the light and the camera are used to determine the location of the board surface by a method such as triangulation. The resulting image represents the range to the board surface and the conveyor. The range image is evaluated using a number of techniques to locate geometric defects such as wane, holes, cracks, skip, scant, bow, etc., which are summarized and preferably passed on to the defect assembler 36.

Moisture

A moisture subsystem (not shown) transmits radio waves through the board. The radio waves are blocked by the water in the wood. The more water there is in the board the more the radio waves are attenuated at the receiver. In this way the moisture profile along the length of the board is determined. Acceptable moisture levels are used to determine what part of the board is likely to be wet, and is to be cut out and/or sorted for further drying or some other type of processing.

Fluorescent Mark

A fluorescent marks reader subsystem (not shown) detects crayon marks placed on the wood surface. These marks can be used to indicate special grade zones to the optimizer 38. As the board passes through the scanner 100 this system detects the crayon mark locations along the length of the board, and summarizes and passes this information to the defect assembler.

Other Sensor Sub-Systems

Other sensor subsystems, both existing and prospective, can be used in the system 10 of the present invention. For example, the three dimensional color imaging system disclosed in U.S. Pat. No. 5,708,498 to Rioux et al can be employed to essentially replace the two separate Profile and Vision sensor subsystems.

Defect Assembler

The defect assembler 36 collects all of the board feature and defect information from the sensing subsystems 100 and adds them together into a single board model for the optimizer to evaluate. More than one sensing subsystem can detect the same defect type and it is the defect assembler 36 that referee's and decides how to summarize the information in the most meaningful manner.

Scheduler

The scheduler (not shown) controls the production and inventory levels by monitoring the production of each product. The current production levels are compared with the order size to be filled and the current recovery of the product for the raw material being processed. This comparison is used to adjust the product weighting so that the order is filled without overproducing the product. This affects the product values used by the optimizer. The scheduler can be incorporated into the host 46.

Optimizer

The optimizer 38 uses a model of each board prepared by the defect assembler and a set of product definitions and cut order to determine the best way to cut the board into product components. The optimizer can be configured for each defect type and size category to expand the defect bounds to ensure that the defect fringes are not included in "good wood." Once these "back offs" have been applied to the defect, the optimizer starts fitting the longest and highest valued products that it can into the board based on the board size, wane profile, and defect locations. This process continues until the defined products have been considered and then the combination that results in the highest volume or value is determined. The decision is then passed to the host 46, graphical user interface 44 or 45, and control subsystems 138. Alternately, a report may be produced which can accompany the boards if sold or sent to another location for processing. Additionally, the resulting decisions from the optimizer can be saved on a computer readable medium and sold with the boards in order to enable the buyer to optimize yield or value from the purchased boards, or to enable a potential buyer to determine the value of the boards. The optimizer results, if stored on a computer readable medium, can also be modified according to factors not within the scope of the optimizer's optimization program. All of the optimizer functions can be accomplished by a computer program or programs. Such optimizers and optimizer programs are known in the art and will not be described further herein.

Control

The control subsystem 138 of FIG. 2 tracks each board as it passes through the system, conveys the board decisions to the appropriate saws, and interfaces with the material handling process control system. Data processing elements of the control subsystem can be incorporated into the host 46.

Programmable Logic Controller (PLC)

Once the optimizer has made a decision regarding a particular workpiece, the decision is preferably communicated to the programmable logic controller (PLC) 42 for execution. The PLC 42 preferably includes computer readable medium for storing computer programs. Examples of computer readable medium include, without limitation, ROM, RAM, a hard drive, a diskette and diskette drive, a CD ROM and CD drive, a tape and tape drive, and an EPROM. The logic controller 42 can decide whether the board is to be cut or not, and if so, by which saw. Typically a plant for processing boards has a plurality of computer controllable saws. Such ensures that the sawing of the boards do not become a bottleneck for throughput through the plant. Further, depending on the type of cut to be made (for example, rip or cross-cut), one saw may be preferably configured over the other. Boards can be routed to a selected saw via a conveyor interchange (not shown) which can be for example a pneumatically actuated conveyor interchange system actuated by the PLC 42. The conveyor interchanger can move a workpiece from a first conveyor to a second conveyor.

Host

The host subsystem 46 comprises a computer-readable medium such as a hard drive, and acts as an "information warehouse" to store the product definitions and save the board production statistics. The host subsystem controls the other subsystems and monitors their status. An uninterruptible power supply preferably communicates with the host, informing of a pending loss of power with enough time to save working data and shut down the system securely. A service modem access can be connected to the host permitting remote diagnostic and troubleshooting, and allowing software upgrades to be transferred to the system from remote locations.

The host or network server 46 can also perform other known functions such as communication with remote devices through modem 48, and interfacing with other computer systems in the sawmill or other facilities through line 360. For example, the network server 46 can provide production information to an accounting or shipping office.

It should be appreciated that the control system, including the DFA 36, the PLC 42, the control module 38, and the host 46 can be considered as a "computer." Alternately, each of the components such as the DFA 36, the PLC 42, the control subsystem 38 module and the network server 46 can also properly be considered separately as computers. While the control scheme is describe herein in a particular configuration, it should be appreciated by one skilled in the art that the necessary functions of the invention, as described fuller herein below, can be accomplished with any one of a variety of control system configurations.

Graphical User Interface (GUI)

The graphical user interface 44 and 45 allows a human/machine interface with the system. Each board decision can be displayed on the GUI as it is processed, with the capability of displaying prior board decisions. The GUI can also display boards with their solutions based on where they are in the material handling system at any given moment. Production reporting, diagnostics, setup, and alarm monitoring can all be handled through the GUI. The system preferably supports multiple GUI's simultaneously, permitting the machine operator to view real-time decisions at the machine while a supervisor can define products from an office off the shop floor.

Board Tracking Apparatus

Since inspection of the board by the system results in a board model having spatial reference to locations on the board, it is important to have a reference point on the board when scanning the board such that the physical measurements accurately represent the board in the board model. Further, when the board is provided to alternate systems, as for example a computer controlled saw, it is important that the board be capable of being aligned such that a board defect in the physical board which is represented in the board model is accurately located with respect to the saw such that optimization decision are effectively carried out by the saw. Data from the tracking system is provided to the control system 38 of FIG. 2. Preferably, the system 10 is provided with a plurality of tracking devices such that the location of a workpiece within the system can generally be known at any time, as well as specifically known within a subsystem itself, as for example within the sensor subsystems 100 or the saw 50.

Figure 11B:
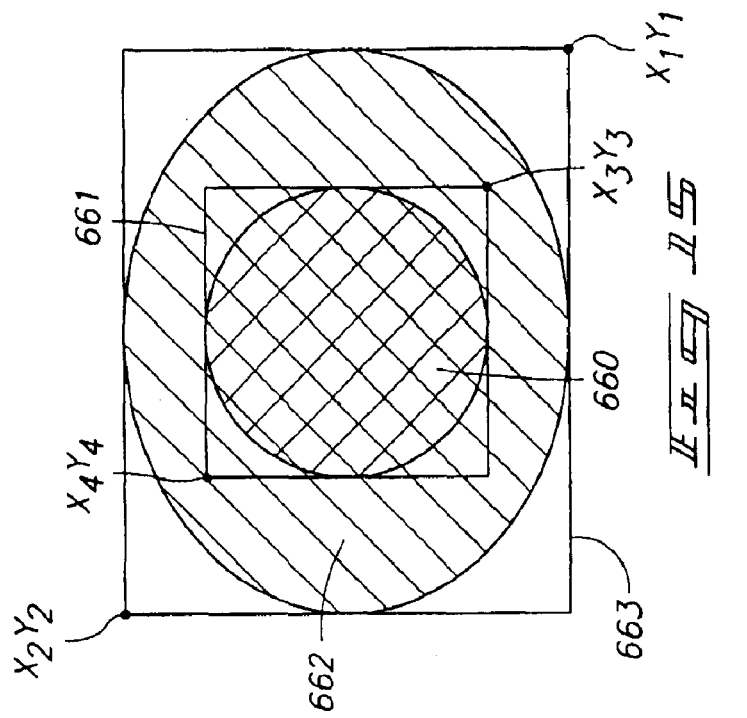
FIG. 11 is a plan view of the board tracking device of FIG. 10.
Figure 11A:
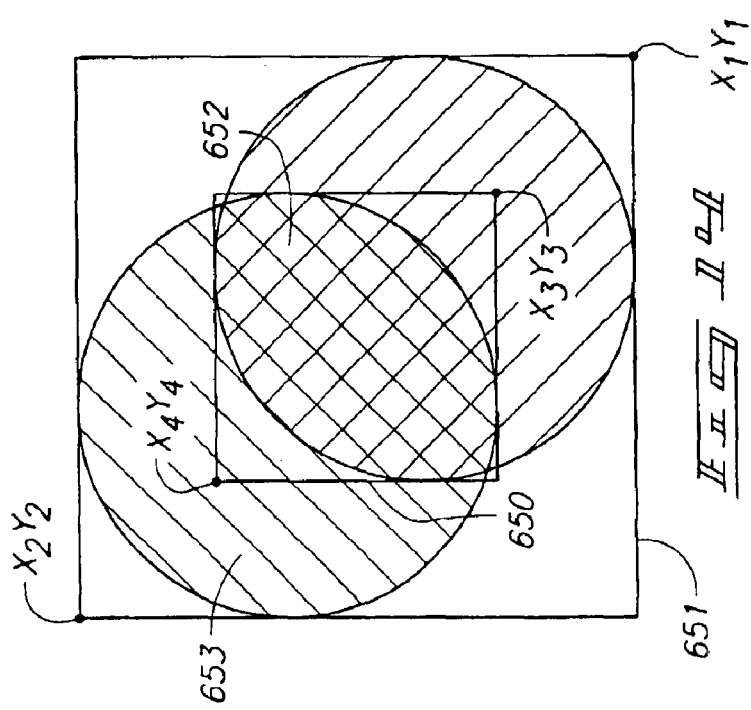

One method of tracking the board is with a laser dopler velocimeter 136 of FIG. 1. Such are available for example from Canon as model LV-20Z. The laser dopler velocimeter permits contact-free measuring of the velocity of the board within the system, movement distances of the board, speed irregularities, and rotation irregularities. Contact-free measurement of the parameters outlined is desirable since contact tracking devices can be prone to slippage or other mechanical problems. An alternate workpiece tracking apparatus is shown in FIGS. 10 through 12. FIG. 10 shows a side elevation view of the apparatus which comprises a plurality of encoder wheels 20. Encoder wheels are configured such that a rotation of the wheel produces a signal, preferably a digital signal, which can be provided to the control subsystem 38 of FIG. 2. In operation, a encoder wheel is in contact with a workpiece and the workpiece is moved past the encoder wheel. The friction of the workpiece on the encoder wheel causes the encoder wheel to rotate. Since the outside diameter of the encoder wheel 20 is known, travel of the encoder wheel over a workpiece can be measured by the number of rotations or partial rotations of the encode wheel, and converted into a lineal distance.

In order to reduce the potential slippage between the encoder wheels 20 and the workpiece, the apparatus 250 is preferably provided with a mechanism for driving the encoder wheels at speed approximating, but slightly less than, that at which the workpiece is expected to move across the encoder wheels. In this manner the encoder wheels have only a slight differential driving force applied to them by the workpiece, reducing wear on the encoder wheels and slippage which can contribute to error. Preferably, the encoder wheels 20 are provided with a unidirectional clutch (not shown) allowing the encoder wheels to be driven at a predetermined minimum percentage of the corresponding speed of the belt 16, but not less than this speed. Thus, if there is slippage of the board relative to the belt 16, the encoder wheels will still rotate at the predetermined percentage. If the board is moving faster than the predetermined minimum percentage of the corresponding speed, the encoder wheels will track the faster velocity.

The mechanism for driving the plurality of encoder wheels is shown in FIG. 11. An electric motor 22 drives a series of belts 138. The belts are attached to pulley assemblies 150. The pulley assemblies are driven by the belt 138 at a first end and have the encoder wheel 20 at a second end. Turning to FIG. 10, the belt and pulley assembly 150 is shown in side view. Preferably, the first pulley 142 drives the encoder wheel 20 by a secondary belt 146. The pulley assembly 150 comprising pulley 142, encoder wheel 20, and secondary belt 146 is configured to pivot about pivot point 152. In this manner, the encoder wheel 20 can move through an arch to effectively raise and lower the encoder wheel, allowing the encoder wheel to encounter workpieces of varying thicknesses and to maintain contact with the board notwithstanding height irregularities in the board surface.

Belts 138 are preferably provided with tensioners 166 as shown in FIG. 10. Since rotation of the encoder assembly 150 about pivot point 152 can alter the geometry of the belt 138 and produce slack in the belt, tensioners 166 are provided to ensure that the drive belts maintain the proper tension against the pulleys 142 during such rotation.

In order to accommodate various heights of boards which can be encountered by the tracking mechanism, the tracking mechanism 250 can be provided with a manual board height adjustment mechanism comprising linkage 19 which, when moved to the left as shown in FIG. 10, causes the encoder wheel 20 to pivot about the pivot point 152, thereby raising the encoder wheel relative to a workpiece on conveyor 14. In one embodiment the linkage 19 is manually adjusted to accommodate a know height of boards to be encountered by the tracking apparatus 250. In a preferred embodiment, the tracking apparatus 250 is provided with an automatic actuating mechanism to automatically raise the encoder wheels 20 to a height approximating that of the workpiece as the workpiece approaches the apparatus 250. The automated actuating mechanism can comprise a photoeye 21 which is attached to a cylinder 156 having a piston 154. Attached at a second end of the piston 154 is a linkage 19 which is attached to the encoder wheel assembly 150 in a manner such that as the piston 154 is retracted into the cylinder 156, the linkage 19 moves to the left as shown in FIG. 10, causing the encoder wheel 20 to pivot about the pivot point 152, thereby raising the encoder wheel relative to a workpiece on conveyor 14. The amount of retraction of piston 154 into cylinder 156 is governed by the photoeye 21 which determines the height of the workpiece.

Turning to FIG. 12, the tracking apparatus 250 is preferably mounted at an angle with respect to the grade 2 such that a workpiece supported on conveyor 14 is urged by gravity towards fence 16 against which the workpiece can rest. This assures that he workpiece will be oriented to a fixed plane, being the fence 16, as it passes through the sensor system. Such essentially establishes a "y=0" reference point for the (x, y) Cartesian coordinate system used to generate the board model.

Returning to FIG. 10, in the preferred embodiment the tracking apparatus 250 comprises a feed conveyor 158 which urges a workpiece toward the sensor system 30, an intermediate conveyor 162, and a discharge conveyor 164. This allows the first conveyor 158 to be separated from the intermediate conveyor 162. Separation of the conveyors can be useful in providing a separation between workpieces to allow a photoeye or other detection system to determine the leading edge of the workpiece.

In an alternate embodiment, a laser dopier tracking device and the tracking apparatus 250 may be used together to confirm each other.

Defect Assembler (DFA)

The defect assembler (DFA) 36 of FIG. 1 is driven by a computer program which is configured to perform the necessary functions of the board model assembler. The purpose of the DFA subsystem is to build a board model using information (for example, the defect and profile list) from any number and combination of sensor subsystems, including a single sensor subsystem. When a single sensor subsystem is employed, it is more appropriate to refer to the defect assembler subsystem as a "data modeler", since it uses data (albeit from a single sensor subsystem) to model a board. In the following discussion, the expression "defect assembler" or "DFA" may be used to refer to the program which drives the defect assembler subsystem. "DFA" or "defect assembler" will also be understood to include a data modeler in a single-sensor or no-sensor configuration.

The defect assembler program is constructed in a classical "producer-consumer" architecture, wherein certain subsystems are producers of information and other subsystems are consumers of information. For example, sensor subsystems 110, 120 and 130 are considered producer subsystem since they produce information relating to the physical attributes of the board, while the saw is a consumer of information since it uses or consumes the board model to cut the board into finished product. Some components, such as the defect assembler, are both producer and consumer. That is, with respect to the defect assembler, it consumes the information produced by the sensing systems and produces a board model which is used by other subsystems. The defect assembler (DFA) functions primarily as a consumer of incoming data from scanning subsystems and as a producer of board model data to subscribers, including the optimizer subsystem (OPT).

As boards travel through a scanner, each scanning subsystem generates a list of defects and other attributes to describe the board. These lists are sent to DFA 36 where they are combined into a single board model. The board model is then passed from DFA to OPT 38 where the "best cut" solution is determined. The DFA 36 is configured to generate board models from any combination of scanning subsystem data produced in the system. In some cases, more than one scanning subsystem will report the same defect. It is the responsibility of DFA to rationalize these instances into the single board model according to a set of arbitration rules.

The DFA's hardware consists of a processor, preferably one having multiple network connections to other subsystems. An exemplary operating system is Windows NT available from Microsoft Corporation.

Board Model Framework

The foundation of the defect assembler subsystem's operation lies in a board model framework that is common to the defect assembler subsystem and the various scanning subsystems. The board model geometry is a combination of three-dimensional (x, y, z) Cartesian coordinates and two-dimensional (x, y) and (x, z) coordinates with reference to the board face as shown in FIG. 5.

The principle of datum referencing is used to relate geometrical features to the reference surface of the ideal board model, and maintain functional similarity of the scanning subsystems to the saw. A datum indicates the origin of a dimensional relationship between a tolerance feature and a reference surface of the wood, i.e., bottom, port, and lead side. The reference surface serves as a datum feature, whereas its true geometric counterpoint establishes the datum.

FIG. 5 illustrates the construction of reference surfaces defined by the scanning system datum. The continuous belt conveyor 14 of FIG. 1 is a datum plane establishing the bottom surface, the fixed fence 18 of FIG. 1 is a datum plane establishing the port surface, and the photoeye 34 is a datum line establishing the lead surface of the board model. The photoeye datum line also establishes the trail surface of the board model, as further described below.

The true geometry of the board referenced from the three datums defines the board model as follows: Three-dimensional Cartesian (x, y, z) coordinate system referenced to lead surface, bottom surface and port surface whereby the origin is the hypothetical intersection of the these three surfaces. Visually, the coordinate system is determined by looking into the scanner from the outfeed, assuming that the board contacts the belt and fence at this point, and applying the "right hand rule" for x, y and z coordinates along the line where the fence and conveyor meet, as indicated by the axes in FIG. 5. At least six two-dimensional faces (top, bottom, port, starboard, lead, trail) comprise a volume describing length, width, and thickness of the board model in x, y, and z Cartesian space, respectively. Leading and trailing faces of the board are defined here for future use. An ambiguous volume within the board (internal) where only two Cartesian coordinates are known (usually x, y) and thickness is defined externally as nominal. Base line dimensioning is used for all coordinates with respect to the datum origin.

The photoeye datum line is preferably used to establish both the lead and trail surfaces of the board model. Each subsystem can receive the photoeye hi/lo signal and the encoder pulses from the conveyor. The photoeye 34 will transition from lo/hi to hi/lo (or visa versa) when a moving board breaks the photoeye beam. Each subsystem will define the lead surface and coordinate origin from this mark. Encoder pulses are recorded and used to measure the distance the conveyor moves the board for a given constant conveyor speed. The photoeye will transition from hi/lo to lo/hi (or visa versa) when the board passes the photoeye and the beam is restored. Each subsystem will define the trail surface and total length from this mark. Because each subsystem preferably measures board length the same, i.e., according to the precision of the encoder pulse train, each subsystem passes a standardized total board length to the defect assembler subsystem.

The photoeye (34 of FIG. 1) is preferably upstream of the sensor subsystems 110, 120 and 130, and each subsystem preferably uses encoder pulses to determine the board lead surface with respect to the constant conveyor speed. That is, as the board moves along the conveyor, each subsystem can determine when the board lead surface passes through the scanning apparatus and when to begin recording data by offsetting the virtual lead surface a pre-defined number of encoder pulses.

If a subsystem determines that a board's lead surface has slipped ahead or behind the expected or virtual lead surface, the subsystem preferably does not re-position the board's lead surface or origin to the determined mark. Preferably, the subsystem will begin sending board data at the determined mark with coordinates referenced to the expected or virtual origin. That is, board data may have negative x-axis coordinates. In addition, the subsystem will preferably record the difference between the mark and the expected lead surface as pre-slippage. If a subsystem determines that a board's trail surface has slipped ahead or behind the expected or virtual trail surface, the subsystem will preferably not re-position the board's trail surface to the determined mark, but will instead continue sending board data after the expected or virtual trail surface, and will also record the difference between the mark and the expected trail surface as post-slippage. The total board length as determined by counting encoder pulses preferably will not change; total length is a data parity check for out-of-sequence defect recognition.

Preferably, each subsystem records the maximum amount of data obtainable for each board. The defect assembler subsystem arbitrates differences in measurements when building the board model from each subsystem's data. The defect assembler subsystem uses pre- and post-slippage information when combining defects from different subsystems and when adding buffer zones around defect features.

Each subsystem preferably sends the defect assembler subsystem exact measured coordinates with respect to the coordinate system described above. Other than mechanical board handling, which is assumed to be similar to the saw, a subsystem preferably does not remove board warp, bow, twist, or cup geometry to produce similitude with nominal board dimensions, nor does a subsystem add buffer material to defect features. Each subsystem preferably measures and bounds features as closely as possible, within the constraints of the subsystem. Note that each subsystem preferably removes measurement distortion effects, for example, x-ray point-source triangulation through the board center and lens barrel correction on the board surface.

Depending on the sensing method at each scanner and what is necessary for optimization, feature coordinate locations may be described in any of the following ways: (1) three-dimensional coordinates in (x, y ,z) format; (2) face and two-dimensional coordinates in (port, x, z), (top, x, y), (starboard, x, z), (bottom, x, y), (lead, y, z), or (trail, y, z) format; or (3) unknown volume and two-dimensional coordinates in (internal, x, y) format. This last model facilitates the combination of two-dimensional data from subsystems including the vision subsystem, the x-ray subsystem, and the moisture subsystem, with three-dimensional data from the profile subsystem. Because the coordinates available from a given scanning subsystem are typically fixed, some of this information is not required in data lists sent to the defect assembler subsystem. For example, all defects bounded by the x-ray subsystem are described in the board model as (internal, min. $x_1$, min. $y_1$, max. $x_1$, max. $y_1$, min. $x_2$, min. $y_2$, max. $x_2$, max. $y_2$) where the z value (internal) remains constant. Therefore, the z value is implied and not sent from the x-ray subsystem for each defect element, but is assumed to be nominal thickness at the defect assembler subsystem when constructing the board model without z data from other scanning subsystems.

Defect coordinate information from each subsystem is defined in FIGS. 3, 5, and 14 and as follows:

| Type | Implied | Sent |
| --- | --- | --- |
| all XRY defects | internal | type, $(x_1, y_1)$, $(x_2, y_2)$ |
| profile data from PRF | x value same for all x, $y_1$, 8 (y, z) pairs | $z_1, y_2, z_2, y_3, y_3, z_3, y_4, z_4,$ $y_5, z_5, y_6, z_6, y_7, z_7, y_8, z_8$ |
| face defect data from PRF | none | type, face (top, bottom), min. x, min. y, max. x, max. y |
| all VIS defects | none | [type, face (top, bottom), min. x, min. y, max. x, max. y] or [type, face (port, starboard), min. x, min. y, max. x, max. y] |
| all MST defects | internal | type, min. x, min. y, max. x, max. y |

Defect Model Definition

The defect assembler subsystem preferably combines 2 and 4-point surface and internal defect boxes of the same type, defined in the above table, into a single defect set. If two or more defect types occupy the same coordinates, e.g., a split inside a knot, two or more defect sets will be defined to represent each defect type so no information is lost. In the case of a boundary dispute, i.e., when one Or more subsystem reports a maximum or minimum boundary different from the principle boundary, the subsystem with the highest basic resolution as determined by the host will prevail.

Because most defects in boards are elliptical in nature, each subsystem preferably minimizes the non-defect wood included as a defect and preserves the true geometry of the defect. Preferably, no subsystem performs defect grouping operations. Each subsystem is preferably configured to convey as much information possible about the true defect shape to the defect assembler.

Board Model Definition

The defect assembler subsystem subscribes to subsystem data as instructed by the host. All subsystem's board data is preferably provided to the defect assembler subsystem in asynchronous frames. A frame is a contiguous length of analyzed area of a scanned board. For example, the first frame of data the defect assembler subsystem could receive contains a surface feature box located at (top, 105.0, 8.0, 106.0, 9.0) and the second frame could contain (top, 10.0, 6.0, 11.0, 7.0). The defect assembler subsystem can provide a board model divided into frames or, less preferably, can hold or buffer the frames until all subscribed subsystem frame data is received. Providing aboard model by frames allows for faster processing of the data. Note that frames may be overlapped for verification purposes and other data processing conveniences. The defect assembler subsystem will then combine the subsystem frame data into the standardized board model and release board model frames to all subscribed consumers.

The defect assembler subsystem advantageously combines and arbitrates frame data according to a hierarchy determined by the host. Frame data includes subsystem features of the outside 8-point profile box of FIG. 4, for each frame sent from each subsystem. The hierarchy of defect combination is as follows:

(1) If a subsystem subscription fails or frame data is not sent within the allotted time limit, a "critical error" message is sent, and the DFA goes to a command state, waiting for intervention. If any single subsystem fails, the defect assembler subsystem issues an alarm to the host and stops processing.

(2) The subsystem with the higher pre-configured hierarchy determines the feature boundary for the board model.

(3) The subsystem with the greater feature recognition reliability determines the presence of a feature. For example, if the vision subsystem determines a knot defect but the x-ray data does not correlate the existence and the host's hierarchy is the x-ray over the vision subsystem, and the vision subsystem defect is not included in the board model.

Releasing a Board Model to "Consumers"

The defect assembler subsystem advantageously issues the board model in frames of contiguous length. The frames are numbered in consecutive order starting with Frame#1 containing the (0, X, X) origin or lead surface. A frame is generated when a section of contiguous length is collected from all subsystems; frame length is determined by the subsystem issuing the shortest-length board frame. If a consumer misses a board frame, the board model cannot be assembled, and a time-out occurs to stop DFA activity. If a consumer misses the last frame closing the board and the allotted time to process the board expires, the consumer is responsible for issuing alarm events and handling real-time operations. The defect assembler subsystem advantageously saves the raw data and board model from each subsystem in a memory device such as a virtual FIFO board queue as blocked threads. Saved data can facilitate debugging of the system and allow simulation of alternative solution methods.

Defect Assembler Subsystem (DFA) Interface

The defect assembler subsystem operates as both consumer and producer of information, as described below under the section about the subsystem interface. As a consumer, the defect assembler subsystem subscribes to data from any combination of scanning subsystems including the x-ray subsystem, the profile subsystem, the moisture subsystem, and the vision subsystem. The defect assembler subsystem also subscribes to board identification data from the controls subsystem. As a producer, the defect assembler subsystem provides board models to subscribers including the optimizer subsystem for cut solution processing, and to the host subsystem for saw outcome simulations.

Scanning Subsystem Interface Requirements

The defect assembler subscribes to measurement and defect data from each available scanning subsystem in the saw optimizer. Because the sensing technology among scanning subsystems is inherently different, it is desirable to standardize their output and facilitate board model assembly. To accomplish this, each scanning subsystem preferably produces data using the coordinate system described above. Additionally, each scanning subsystem preferably provides three basic data subscriptions to the defect assembler subsystem including defect, dimension, and profile categories (as indicated in FIG. 3), for each scanning subsystem. Basic requirements for these subscriptions are as follows.

Defect Category

Each scanning subsystem is advantageously capable of reporting certain defect types. Some defect types can be measured by multiple scanning subsystems (e.g. the vision subsystem and the x-ray subsystem both report knots) while others can only be detected by a single subsystem. Regardless of defect type, a common structure is used be used when sending these data to the defect assembler subsystem. Defect coordinates define a bounding box containing two or four non-zero points depending on the type of defect and sensing ability of the scanning subsystem.

Two-Point Bounding Box

Two points are used to define a single box containing the entire defect. For example, in FIG. 5, $x_2z_2$ and $x_1z_1$ points define the upper-left and lower-right corners (with respect to the figure view) of the entire box 340. This method is sufficient for defects where varying degrees of severity are not useful during optimization. In FIG. 5, box 340 shows blue stain defect that is entirely bounded by the defect box on either the port or starboard board face. The box 310 shows a knot with grain swirl entirely bounded on either the top or bottom board face.

Less preferably, four points can be used to define an outer box containing the entire defect, and an inner box containing a region with significantly different defect attributes such as grain swirl or density. Referring to FIGS. 14 and 15, points $X_1Y_1$, $X_2Y_2$ define the outer box while points $X_3Y_3$, $X_4Y_4$ define the optional inner box. While computationally more complex, this method of defect bounding can provide better calculation of three-dimensional defects, such as spike knots, and maximum optimization of possible cut products.

For the x-ray subsystem, inner and outer box classification is preferably obtained using two threshold levels. Using two threshold levels also increases the certainty of correctly bounding the geometry of solid defects because denser core material is tightly bound by the inner box thus permitting fast detection of defects with fixed thresholding. Less dense cross grain around knots is bound by the second outer box thus allowing more accurate, localized, statistically-adaptive thresholding. In FIG. 14, a spike knot defect is shown where the inner box 650 bounds defect material 652 which is solid through the entire thickness of the board and the outer box 651 bounds material 653 which is less dense. FIG. 15 shows a straight knot 660 bound by the inner box 661 and less dense cross grain 662 bound by the outer box 663. FIG. 5 shows a solid dense defect 370 having non-determinable cross grain (perhaps from a rapid growth tree) and is bound by a single box 310. For the vision subsystem, four points are preferably used to define knot-type defects comprising solid defect (knot) material and cross grain. Two-point boxes are preferably used for all other defects. An outer box bounds the entire defect, and an inner box bounds the knot. As in FIG. 14, points $X_1Y_1$, $X_2Y_2$ define the outer box while points $X_3Y_3$, $X_4Y_4$ define the optional inner box. This method of defect bounding allows better calculation of three-dimensional defects and maximum optimization of possible cut products. For visual subsystem, FIG. 14 shows a straight knot 652 bound by the inner box 650 and less dense cross grain bound 653 by the outer box 651. FIG. 5 shows a solid dense defect 370, such as a ring knot, having non-determinable cross grain and is bound by a single box 310.

Profile Category

Each scanning subsystem is configured to be capable of measuring board profile to some extent. Because of differences in scanning technology, there is significant variance among the subsystems ability to measure profile in all planes and their relative resolutions. Regardless of these differences, a common structure can be used when sending these data to the defect assembler subsystem. Profile data are measured at regular x-axis intervals, or cross sections of the board. At each cross section, the subsystem determines an eight-point structure that describes board profile according to the following rules:

(1) All data points preferably follow the datum-referenced Cartesian coordinate system defined above.

(2) A flat segment is defined as planed and roughly vertical or horizontal. Some angular variance is expected in boards With twist, warp, and/or cup.

(3) An irregular segment is defined as not planed, even though it may be reasonably flat.

Figure 6:
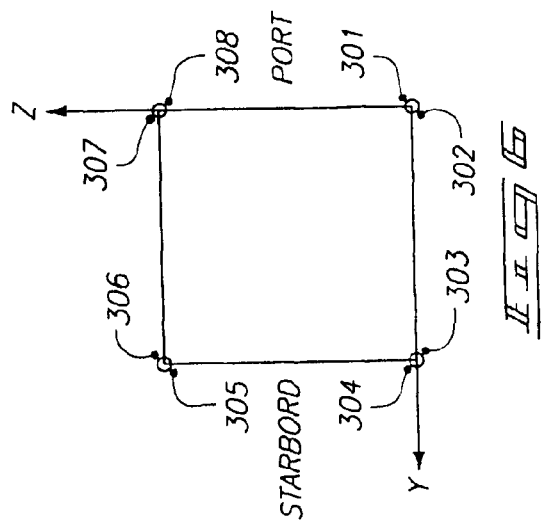
FIG. 6 is an end view diagram of the board model of FIG. 5 wherein the corner vertices collapse for a rectangular board.

(4) A vertex is defined as the transition point between either two flat segments, one flat segment and one irregular segment, the widest point at which an irregular outside segment (port or starboard) has vertical slope, the thickest point at which an irregular top or bottom segment has horizontal slope, or the thinnest point at which an irregular top or bottom segment has horizontal slope. Vertex examples are shown in FIGS. 5, 6 and 7.

(5) Eight (8) vertexes can be used to describe the board profile at a given x location as shown in FIG. 5.

(6) Vertexes 1 through 4 are defined from bottom scanner data, and vertexes 5 through 8 are defined from top scanner data.

(7) Vertex numbering begins with the origin (x=0, y=0) coordinate and proceeds counter-clockwise to describe all coordinates. If a board is twisted, numbering begins with the bottom scanner's vertex closest to the fence datum and not defined by the top scanner's vertex.

(8) All vertexes are used.

(9) Linear interpolation to the basic resolution is allowed between all data points.

Once the eight-point perimeter has been determined, it is described in a dimension data structure.

When a given subsystem (the x-ray subsystem, for example) cannot measure all portions of the complete profile data set, nominal values are substituted in those fields before being sent to the defect assembler subsystem.

Dimension Category

Each scanning subsystem is preferably configured to receive identical scanner encoder and photoeye information. Therefore, each scanning subsystem will "measure" standardized gross board lengths. It is possible for a scanning subsystem's own sensors to report lead and trail board edges that are different from those reported by the photoeye and encoder. The defect assembler subsystem handles these cases separately. In addition to gross length, scanning subsystem can report to the defect assembler subsystem the gross width and gross thickness of each board. When these quantities can be directly measured, the measurements are used. Otherwise, nominal width and thickness values are used.

Data Flow

Under normal operation the defect assembler subsystem offers services to the following subscribers: optimizer (OPT); and host (HST).

Under normal operation the defect assembler subsystem subscribes to services from. the following producers: vision (VIS); x-ray (XRY); profile (PRF); and moisture (MST). The defect assembler subsystem external data flow is generally depicted below in FIGS. 2 and 13.

The following services allow other subsystems to subscribe to, or request data from the defect assembler subsystem.

Board model rules are used to control how the defect assembler subsystem will process lumber from various board quality or stock grades. For example, users might choose to place less confidence in knot boundaries reported by the vision subsystem in certain types of lumber because they know that the x-ray subsystem will do a better job of bounding these defects. The solution is to develop a list of defect assembly rules for that paradigm which will produce the correct board model. The types of rules can comprise the following: hierarchy used to select best profile measurements when in conflict; valid defect types used to build board model from subsystem information; hierarchy used to select best defect measurements when in conflict; probability that standard defect has been correctly identified by the specified scanning subsystem; the minimum editable defect; the maximum editable defect; the maximum x-axis separation between defects of same type for grouping into common set; the maximum y-axis separation between defects of same type for grouping into common set; scalable x-axis adjustment to defects reported by the specified scanning subsystem; and scalable y-axis adjustment to defects reported by the specified scanning subsystem.

The following description describes individual functioning units that make up the defect assembler subsystem.

Scanning LAN Interface

A scanning LAN connects the defect assembler to all scanning subsystems including, for example, x-ray, profile, moisture, and vision. The scanning LAN is, for example, an Ethernet network intended primarily to transfer defect list elements from scanning subsystems to the defect assembler. Additional LAN traffic can include pass-through information from a machine center LAN, and board ID messages from machine controls subsystem. The defect assembler gains access to the scanning LAN through a network adapter card. Software access can be provided via TCP/IP and BSD sockets at the operating system level, wherein the connections are preferably message based stream sockets. A board model LAN connects the defect assembler to the optimizer subsystem and machine controls subsystem. The board model LAN is, for example, an Ethernet network intended primarily to transfer board models from the defect assembler to the optimizer, and cut solutions from the optimizer to the machine controls. The defect assembler gains access to the board model LAN through a network adapter card similar to the scanning LAN.

Operation

Under running conditions, the defect assembler subsystem operates per the following description.

For each board processed, the defect assembler subsystem can receive the board identification from machine controls subsystem and the defect list elements and overall length from each sensing (defect detecting) subsystem. For each board processed, the defect assembler produces a board model to the optimizer subsystem and other optional subscribers.

It is the defect assembler's responsibility to track synchronization of each scanning subsystem as boards are processed. If the defect assembler determines that one or more scanning subsystems have failed, a message is sent immediately to the Host Subsystem indicating the nature of the failure.

Synchronization is handled according to the following rules:

(1) When a new Board ID is received from machine controls, the defect assembler creates the new board model list node.

(2) The board-specific node is responsible for receiving and compiling defect elements from each configured scanning subsystem until all defect lists are complete.

(3) A new node may be created before the nodes for the previous (n) boards have completed, where n is configurable.

(4) A node for a new board can be created if the node for board (n-1) is not completed. This indicates a problem and is cause for sending an alarm event to the host.

The following sequence is typical for operations involving a single board:

(1) Board enters scanner and is seen by tracking photoeye.

(2) Machine controls subsystem issues board ID to scanning subsystems and the defect assembler.

(3) The defect assembler creates board model node in the list to generate board model and waits for data from scanning subsystems.

(4) Scanning subsystems send asynchronous messages containing defect elements and overall board length. The defect assembler generates board model as defect elements arrive.

(5) When the defect assembler receives overall board length from all operating scanning subsystems, board model is completed and the node is removed from the list.

(6) The defect assembler sends board model to subscribers.

Due to the asynchronous nature of incoming defect data and variable processing delays from each scanning subsystem, the defect assembler preferably is capable of overlapping the above sequence for multiple boards.

Conflict Resolution

Depending on the configuration of scanning subsystems, the defect assembler subsystem may receive conflicting information from two or more sources. For example, the x-ray subsystem and the vision subsystem are both capable of detecting knots but are unlikely to bound a given knot with identical coordinates. The following description outline rules used by the defect assembler subsystem to resolve defect data conflicts during board model assembly.

Knots:

Most knot boundary conflicts will arise from differences between the vision subsystem and the x-ray subsystem data. A small number of knots exhibiting tear-out might also be detected by the profile subsystem as face defects, but probably won't be classified as knots. In order to define conflict resolution rules between the vision subsystem and the x-ray subsystem, it is important to understand relative performance advantages of each subsystem. For example, the x-ray subsystem has the highest certainty of detecting absolute knot presence, but is less capable of correctly bounding knots due to an inability to "see" surrounding grain swirl and differentiate between opposite board faces. Conversely, the vision subsystem has lower certainty of detecting knot presence because of false readings caused by heavy grain patterns or foreign matter on the board surface, but has greater ability to measure grain angle and detect boundaries on any board face. Based on these considerations, rules for adding knot defects to the board model can be developed. For example

| Seen by X-ray | Seen by Vision | Resolution |
| --- | --- | --- |
| Yes | No | Knot is added to board model with identical top and bottom boundaries as reported by x-ray. |
| Yes | Yes | Knot is added to board model with all face boundaries as reported by vision. |
| No | No | No knot added to board model. |
| No | Yes | No knot added to board model. |

Implementation

The defect assembler subsystem architecture consists of several threads and their associated functions as shown in FIG. 16 for an x-ray subsystem 820. When a board arrives at the control subsystem photoeye, the defect assembler subsystem 800 receives board identification (ID) data from the control (CTL) subsystem 801. As long as the new board thread 802 receives the board identification data from the defect assembler subsystem's control subsystem consumer call back function 805, it will save the data into the "board processing thread working buffer" 803 and assign a board identification to the waiting board processing thread 804. The board processing thread Will then spawn another board processing thread 806 to wait for the next board.

To minimize the x-ray consumer callback function 809 from being blocked too long by received defect/profile data frames, two named pipes 807 and 808 are used to write received defect/profile data into the named pipes by x-ray consumer callback functions. Two threads, x-ray profile handle 810 and defect data handle 811, are used to read the data from the named pipes, then deposit it into the frame data buffer of the "board processing thread working buffer" 803 and notify the synchronized data dispatcher thread 812 that defect/profile data has arrived. The synchronized data dispatcher thread 812 then verifies that data in the "board processing thread working buffer" 803 is available to be assembled into a board model data frame. The dispatcher thread 812 then moves the available data elements to a synchronized data buffer 821 and sends a semaphore 822 or 823 to the related board processing thread 804 or 806 to notify it that the synchronized data is ready.

While the defect assembler subsystem has multiple board processing capability, preferably only the major board processing thread 804 is configured to construct board model data frames and send them to the optimizer subsystem 813. Other board processing threads 806 and 814 will merge their synchronized data into a temporary board model data buffer and wait for their turn.

The defect assembler subsystem architecture is preferably scalable for future development.

Subsystem Interface

Overview

The subsystem interface (IFC) 200 of FIG. 2 is a mechanism to exchange data between subsystems in a generic, scalable manner. The mechanism is based on a producer/consumer model where one component produces a set of services and other component(s) consume the services. The subsystem interface is composed of a producer API (application program interface) and a consumer API. Both API's are designed for use on a multi-threaded operating system. The producer API consists of routines to initialize the producer server and client objects, receive requests from the consumer, and send acknowledgment and data to the consumer in response to the requests. The consumer API consists of routines to initialize the consumer server and client objects, send requests to the producer, and receive acknowledgment and data from the producer in response to the requests. The subsystem interface functions as a static library to be linked into the subsystems that require data exchange.

The following description is with particular focus on the interface between all subsystems within the saw optimizer, although it is to be appreciated that such reference is for exemplary purposes only, and the general concept can be applied to other subsystems.

Interface

Messages between the producer/consumer components beneficially include a message protocol for message handling. An example of a protocol used in one example is as follows. Each message sent between subsystems beneficially contains a header with the following information: system-wide unique subsystem number; subsystem-wide unique service number; service qualifier (what is being performed (subscribe, unsubscribe, request, acknowledge, reply)); and length of data (in bytes) to follow the header.

The header is created and consumed by the subsystem interface, and defines the data buffer that is exchanged between the subsystems. The subsystem, service, and service qualifier fields together uniquely identify the message in the system. The consumer provides the subsystem, service, and service qualifier values, along with the data and data length to the consumer server. The consumer server packages the subsystem, service, service qualifier and data length values into a header structure and sends it to the producer server. The data is sent to the producer server after the header. The producer server first reads the header to determine the size of the data that follows. The producer server then reads the data into a data buffer. Then the subsystem, service, service qualifier, data, and data length are passed to the producer through the producer callback function. The producer preferably copies the data to its own data space before returning from the producer callback function, as the buffer will be reused on the next data read. The same occurs when the producer sends data to the consumer.

The service qualifier determines what action is to be taken on a service for a subsystem. The action can be one of the following: subscribe to a continuous feed of data; end subscription to a continuous feed of data; request a single reply (oneshot); acknowledge the receipt of a subscribe, unsubscribe, or request (a return status in the data portion determines the success of the action); or buffer containing the results of a subscription or request (a return status in the data portion determines the validity of the data).

A data buffer can be sent with any type of message (subscribe, unsubscribe, request, acknowledge, and reply). The length of the data is set in the dataLen field of the header and can range in value from zero, for no data, to the maximum size expected depending on the service. The amount and structure of the data is determined by the service.

The subsystem interface uses a subscription-based model to send/receive data. A model of this system in shown in FIG. 11. A consumer (e.g., 501 or 502) subscribes to a feed of data from a producer 503. When the producer generates the data, it sends the data to all consumers that have subscribed to that data (if any).

Consumer

The consumer thread 504, 505, or 506 subscribes to data and consumes the data upon reply from the producer 503. This thread must first initialize a consumer client object and attach it to the consumer server object. All subsequent actions (subscribe, unsubscribe, request) require the consumer client object. The consumer may consist of several threads all using one consumer server 507 or 508. In this case, each consumer thread must initialize its own consumer client object to mutually exclude other consumer threads. This method shares one consumer callback function between all consumer threads.

Alternately, each consumer thread create its own consumer server connection to the producer. This method is typically used when the consumers reside in separate tasks or on separate machines and cannot easily share a consumer server. This method causes the producer server to do more work in that it must send data to multiple consumer servers. This method also allows each consumer thread to have its own consumer callback function.

The consumer API 511 or 512 is the Consumer's interface to the message passing mechanism. The Consumer API contains the following set of routines:

Initialize a consumer server object. The consumer server thread is started. A consumer callback function is recorded for use by the consumer server upon receipt of data.

Close the consumer server object. The socket is closed which forces the consumer server to shut down. This routine is called prior to terminating the consumer task.

Initialize a consumer client object. The consumer server object is passed as a parameter in order to link the consumer client object to the consumer Server object. The consumer server object is initialized first. All further actions (subscribe, unsubscribe, request) use this consumer client object. Each consumer thread initializes its own consumer client object in order to mutually exclude each other.

Close the consumer client object. If any subscriptions are still outstanding, they will not be unsubscribed.

Allow the consumer to subscribe to a continuous feed of data from the producer. When the data is generated, the producer will send a reply message containing the data.

Allow the consumer to end subscription of a continuous feed of data from the producer. This is performed before closing the consumer client object.

Allow the consumer to request a oneshot reply of data from the producer. Often this request contains data for the producer to use. The producer sends a reply message in response to the request.

The consumer server 507 or 508 is a thread that is started from an "initialize a consumer service object" API call. This thread monitors the connection status of the socket or data port and receives acknowledge and reply messages from the producer and passes them to the consumer via the consumer callback function 509 or 510. The consumer callback is a function that is used by the consumer server to alert the consumer thread(s) 504 through 506 of receipt of data or change in connection status from the producer server 513. This function is offered by the consumer when initializing the consumer server object. One consumer callback is associated with one consumer server. When data is passed to the consumer callback it is preferably copied to the consumer's space as the buffer is reused when control is returned from the consumer callback.

Producer

The producer thread 514 or 515 replies to subscriptions from the consumer 501 or 502. This thread first preferably initializes a producer client object, via an "initialize a consumer client object" consumer API, and attaches it to the producer server object. All subsequent replies use the producer client object. The producer may consist of several threads all using one producer server 513. In this case, each producer thread 514 or 515 preferably initializes its own producer client object to mutually exclude other producer threads. This method shares one producer callback function between all producer threads.

The producer API is the producer's interface to the message passing mechanism. The producer API contains the following set of routines:

Initialize a producer server object. The producer server thread is started. A producer callback function is recorded for use by the producer server upon receipt of requests.

Close the producer server object. All connecting sockets are closed which forces the producer server to shut down. This routine is called prior to terminating the producer task.

Initialize a producer client object. The producer server object is passed as a parameter in order to link the producer client object to the producer server object. The producer server object is initialized first. All replies preferably use this producer client object. Each producer thread preferably initializes its own producer client object in order to mutually exclude each other.

Close the producer client object.

Allow the producer to reply to a continuous or oneshot subscription to data. If the subscription is a oneshot request, the subscription is removed from the subscription table. This message usually contains data and a return status to qualify the data.

The producer server is a thread that is started from a "initialize a producer server object" API call. This thread monitors the connection status of the data socket and receives subscribe, unsubscribe, and request messages from the consumer 501 or 502 and passes them off to the producer 503 via the producer callback function 516. Upon connection of a consumer server, a new producer server thread is spawned to handle the next consumer server connection. When a connection is broken or dropped, the producer server thread 514 or 515 associated with this connection is cleaned up and terminated. All references to this connection are removed from the subscribe tables 517.

The producer callback 516 is a function that is used by the producer server to alert the producer thread(s) 514 and 515 of receipt of data from the consumer server 507. This function is offered by the producer 503 when initializing the producer server object. One producer callback is associated with one producer server. When data is passed to the producer callback it is preferably copied to the producer's space as the buffer is reused when control is returned from the producer callback.

There are two subscribe tables 517: client and message. The client table consists of information about all consumer server connections. The message table consists of information about all service subscriptions. Together, these tables enable the producer 503 to send reply messages to all consumers 501 and 502 that have subscribed to services.

While the invention is described above as being particular to lumber, it is understood that the invention is equally practical for any workpiece having potential defects, and is particularly practical where such workpieces are non-homogeneous.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A generic, scalable consumer subsystem/producer subsystem interface controller for exchanging data between at least one producer subsystem configured to produce a set of services characterized in a producer generated data set, and at least one consumer subsystem configured to consume the set of services, comprising:

an object-oriented producer application program interface (API) configured for use on a multi-threaded, client-server operating system, comprising producer routines configured to:
  initialize producer server objects and producer client objects;
  receive requests for data from a consumer subsystem via said producer client objects;
  send acknowledgments to a consumer subsystem in response to requests from the consumer subsystem via said producer server objects;
  send data to a consumer subsystem in response to requests from the consumer subsystem via said producer server objects; and an object-oriented consumer application program interface (API) configured for use on a multi-threaded, client-server operating system, comprising consumer routines configured to:
  initialize consumer server objects and consumer client objects;
  send requests for data to a producer subsystem via said consumer server objects;
  receive acknowledgments from a producer subsystem in response to requests from the producer subsystem via said consumer client objects; and
  receive data from a producer subsystem in response to requests from the producer subsystem via said consumer client objects.

2. The subsystem interface of claim 1 wherein at least one of the consumer subsystems comprises a consumer server having a producer subscription to data from at least one of the producer subsystems, the producer API further comprising a first producer server thread configured to first initialize a producer client object and then to reply to the producer subscription by connecting to the consumer server.

3. The subsystem interface of claim 2 wherein the producer API is further configured to generate a new producer server thread for connection to a consumer server upon connection of the first producer server thread to the consumer server.

4. The subsystem interface of claim 3 wherein:
  producer server threads are listed on a subscribe table accessible by consumer servers;
  each producer server thread is disconnectable from a consumer server; and
  upon disconnection of a producer server thread from a consumer server, the disconnected producer server thread is removed from the subscribe table.

5. The subsystem interface of claim 2 wherein the consumer API further comprises a plurality of consumer server threads each configured to create a dedicated connection to a producer subsystem.

6. A generic, scalable method for controlling the exchange of data in a consumer/producer system between at least one producer subsystem configured to produce a set of services characterized in a producer generated data set, and at least one consumer subsystem configured to consume the set of services, comprising:

initializing producer server objects and producer client objects within an object-oriented producer application program interface (API) configured for use on a multi-threaded, client-server operating system;
receiving requests for data from a consumer subsystem via at least one of the initialized producer client objects;
sending acknowledgments to a consumer subsystem in response to requests from the consumer subsystem using at least one of the producer server objects;
sending data to a consumer subsystem in response to requests from the consumer subsystem using at least one of the producer server objects;
initialize consumer server objects and consumer client objects within an object-oriented consumer application program interface (API) configured for use on a multi-threaded, client-server operating system;
sending requests for data to a producer subsystem using at least one of the consumer server objects;
receiving acknowledgments from a producer subsystem in response to requests from the producer subsystem using at least one of the consumer client objects; and
receiving data from a producer subsystem in response to requests from the producer subsystem using at least one of the consumer client objects.

* * * * *